United States Patent
Brown et al.

(10) Patent No.: US 7,960,389 B2
(45) Date of Patent: *Jun. 14, 2011

(54) 4(PHENYL-PIPERAZINYL-METHYL) BENZAMIDE DERIVATIVES AND THEIR USE FOR THE TREATMENT OF PAIN OR GASTROINTESTINAL DISORDERS

(75) Inventors: William Brown, St. Laurent (CA); Andrew Griffin, St. Laurent (CA); Paul Jones, St. Laurent (CA); Daniel Page, St. Laurent (CA); Niklas Plobeck, Sodertalje (SE); Christopher Walpole, St. Laurent (CA)

(73) Assignee: AstraZeneca AB, Sodertalje (SE)

( * ) Notice: Subject to any disclaimer, the term of this patent is extended or adjusted under 35 U.S.C. 154(b) by 599 days.

This patent is subject to a terminal disclaimer.

(21) Appl. No.: 11/774,935

(22) Filed: Jul. 9, 2007

(65) Prior Publication Data
US 2007/0254890 A1 Nov. 1, 2007

Related U.S. Application Data

(63) Continuation of application No. 10/533,654, filed as application No. PCT/SE03/01707 on Nov. 5, 2003, now Pat. No. 7,253,173.

(30) Foreign Application Priority Data

Nov. 7, 2002 (SE) ...................... 0203303

(51) Int. Cl.
*A61K 31/4965* (2006.01)
*A61P 25/22* (2006.01)
*C07D 295/03* (2006.01)

(52) U.S. Cl. .................. 514/255.04; 544/396

(58) Field of Classification Search .................. 544/396; 514/255.04
See application file for complete search history.

(56) References Cited

U.S. PATENT DOCUMENTS

| | | | |
|---|---|---|---|
| 3,940,386 A | 2/1976 | Szabo et al. |
| 4,778,789 A | 10/1988 | Fex et al. |
| 5,574,159 A | 11/1996 | Chang et al. |
| 5,658,908 A | 8/1997 | Chang et al. |
| 5,681,830 A | 10/1997 | Chang et al. |
| 5,807,858 A | 9/1998 | Chang et al. |
| 5,840,896 A | 11/1998 | Van Belle et al. |
| 5,854,249 A | 12/1998 | Chang et al. |
| 6,130,222 A | 10/2000 | Roberts et al. |
| 6,680,318 B2 | 1/2004 | Brown et al. |
| 6,680,321 B1 | 1/2004 | Roberts et al. |
| 6,696,447 B2 | 2/2004 | Brown et al. |
| 6,784,181 B2 | 8/2004 | Brown et al. |
| 7,030,124 B2 | 4/2006 | Chang et al. |
| 7,229,994 B2 | 6/2007 | Brown et al. |
| 7,253,173 B2 | 8/2007 | Brown et al. |
| 2004/0138228 A1 | 7/2004 | Roberts et al. |
| 2006/0030569 A1 | 2/2006 | Brown et al. |
| 2006/0142296 A1 | 6/2006 | Brown et al. |
| 2006/0167004 A1 | 7/2006 | Brown et al. |
| 2007/0249619 A1 | 10/2007 | Brown et al. |
| 2007/0270435 A1 | 11/2007 | Brown et al. |
| 2007/0293502 A1 | 12/2007 | Brown et al. |
| 2009/0291966 A1 | 11/2009 | Frey et al. |
| 2010/0168130 A1 | 7/2010 | Brown et al. |

FOREIGN PATENT DOCUMENTS

| | | |
|---|---|---|
| DE | 2431178 | 1/1975 |
| DE | 2900810 | 7/1980 |
| EP | 0133323 | 2/1985 |
| EP | 0166302 | 1/1986 |
| EP | 0283310 | 9/1988 |
| EP | 0289227 | 11/1988 |
| EP | 0624584 | 8/1998 |
| FR | 2696744 | 4/1994 |
| GB | 2076403 | 12/1981 |
| GB | 2210366 | 6/1989 |
| HU | 215847 | 4/1999 |
| HU | 217619 | 3/2000 |
| JP | 7138230 | 5/1995 |
| WO | 8604584 | 8/1986 |
| WO | 9107967 | 6/1991 |
| WO | 9204338 | 3/1992 |

(Continued)

OTHER PUBLICATIONS

Jones et al, "British Society of Gastroenterology guidelines for the management of the irritable bowel syndrome." Gut 2000, (Suppl II)47:ii1-ii19.*

Adriaensen, H. et al., "Clinical Review of Oral Drug Treatments for Diabetic Neuropathic Pain-Clinical Outcomes Based on Efficacy and Safety Data from Placebo-Controlled and Direct Comparative Studies," Diabetes Metab. Res. Rev., 2005, 21(3), pp. 231-240.

Banker, G. et al., "Modern Pharmaceutics, 3ed.", Marcel Dekker, New York, 1996, pp. 451 and 596.

Bilsky, E. et al., "SNC 80, A Selective, Nonpeptidic and Systematically Active Opioid Delta Agonist," Journal of Pharmacology and Experimental Therapeutics, 1995, vol. 273, pp. 359-366.

(Continued)

*Primary Examiner* — Susanna Moore
(74) *Attorney, Agent, or Firm* — Woodcock Washburn LLP

(57) ABSTRACT

Compounds of general formula:

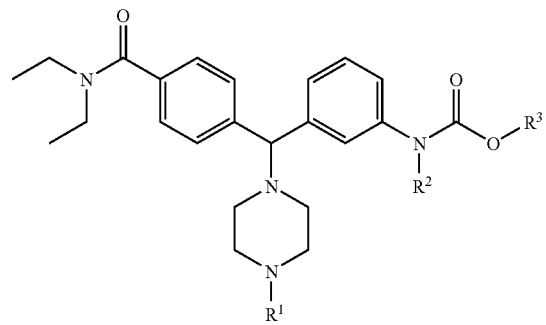

wherein $R^1$, $R^2$ and $R^3$ are as defined in the specification, as well as salts, enantiomers thereof and pharmaceutical compositions including the compounds are prepared. They are useful in therapy, in particular in the management of pain.

5 Claims, No Drawings

FOREIGN PATENT DOCUMENTS

| WO | 9206971 | 4/1992 |
|---|---|---|
| WO | 9315062 | 8/1993 |
| WO | 9504051 | 2/1995 |
| WO | 9626196 | 8/1996 |
| WO | 9723466 | 7/1997 |
| WO | 9828270 | 7/1998 |
| WO | 9828275 | 7/1998 |
| WO | 9901033 A1 | 1/1999 |
| WO | 9933806 | 7/1999 |
| WO | 0001375 A2 | 1/2000 |
| WO | 0145637 | 6/2001 |
| WO | 0146174 | 6/2001 |
| WO | 0146263 | 6/2001 |
| WO | 0174805 | 10/2001 |
| WO | 02094786 | 11/2002 |
| WO | 02094794 | 11/2002 |
| WO | 02094812 | 11/2002 |
| WO | 03029215 | 4/2003 |
| WO | 03094853 | 11/2003 |
| WO | 2004041800 | 5/2004 |
| WO | 2004041801 | 5/2004 |
| WO | 2004041802 | 5/2004 |
| WO | 2004062562 | 7/2004 |
| WO | 2005066148 | 7/2005 |
| WO | 2006014133 | 2/2006 |
| WO | 2006091160 | 8/2006 |

OTHER PUBLICATIONS

Bilsky, E. et al., "Characterization of Enantiomers of (+)BW373U86 and Related Compounds: Highly Selective Non-Peptidic Delta Opioid Agonists," Regulatory Peptides, 1994, vol. 54, pp. 25-26.

Burkey, T. et al., "The Efficacy of Delta-Opioid Receptor-Selective Drugs," Life Sciences, 1998, vol. 62, Nos. 17/18, pp. 1531-1536.

Calderon, S. et al., "Probes for Narcotic Receptor Mediated Phenomena. 19. Synthesis of (+)-4-[(R)-((2S,5R)-4-Allyl-2,5-dimethyl-1-piperazinyl)-3-methoxybenzyl]-N,N-diethylbenzamide (SNC 80): A Highly Selective, Nonpeptide Delta Opioid Receptor Agonist," J. Med. Chem., 1994, vol. 37, pp. 2125-2128.

Calderon, S. et al., "Probes for Narcotic Receptor Mediated Phenomena. 23. Synthesis, Opioid Receptor Binding, and Bioassay of the Highly Selective Delta Agonist (+)-4-[(R)-((2S,5R)-4-Allyl-2,5-dimethyl-1-piperazinyl)-3-methoxybenzyl]-N,N-diethylbenzamide (SNC 80) and Related Novel Nonpeptide Delta Opioid Receptor Ligands," J. Med. Chem., 1997, vol. 40, pp. 695-704.

Chang, K. et al., "A Novel, Potent and Selective Nonpeptidic Delta Opioid Receptor Agonist BW373U86," The Journal of Pharmacology and Experimental Therapeutics, 1993, vol. 267, No. 2, pp. 852-857.

Davis, MP et al., "Controversies in Pharmacotherapy of Pain Management," Lancet Oncol., 2005, 6(9), pp. 696-704.

Filliol, D. et al., "Mice deficient for delta- and mu-opioid receptors exhibit opposing alternations of emotional responses," Nature Genetics, 2000, vol. 25, pp. 195-200.

Greene, T. et al., "Protective Groups in Organic Synthesis," 1981, pp. 267-268 and 331.

Katrizky, A. et al., "Benzotriazole-mediated Arylalkylation and Heteroarylalkylation," Chemical Society Reviews, 1994, pp. 363-373.

Kingsbury, W. et al., "Synthesis of Structural Analogs of Leukotriene B4 and Their Receptor Binding Activity," J. Med. Chem., 1993, vol. 36, pp. 3308-3320.

Lopez, J. et al., "Exploring the Structure-Activity Relationships of [1-(4-tert-Butyl-3'-hydroxy)benzhydryl-4-benzylpiperazine] (SL-3111), a High-Affinity and Selective Delta Opioid Receptor Nonpeptide Agonist Ligand," J. Med. Chem., 1999, vol. 42, pp. 5359-5368.

Nagase, H. et al., "The Pharmacological Profile of Delta Opioid Receptor Ligands, (+) and (-31 ) TAN-67 on Pain Modulation," Life Sciences, 2001, vol. 68, pp. 2227-2231.

Nortey, S. et al., "Piperazinyl Benzamidines: Synthesis and Affinity for the Delta Opioid Receptor," Bioorganic & Medicinal Chemistry Letters, 2001, vol. 11, pp. 1741-1743.

Plobeck, N. et al., "New Diarylmethylpiperazines as Potent and Selective Nonpeptidic Delta Opioid Receptor Agonists with Increased in Vitro Metabolic Stability," J. Med. Chem., 2000, vol. 43, pp. 3878-3894.

Przewlocki, R. et al., "Opioids in Neuropathic Pain," Curr. Pharm. Des. 2005, 11(23), pp. 3013-3025.

Saitoh, A., "Potential anxiolytic and antidepressant-like activities of SNC80, a selective delta-opioid agonist, in behavorial models in rodents," J. Pharmacol. Sci., 2004, vol. 95, pp. 374-380.

Snyder, S. et al., "Historical Review: Opioid Receptors," TRENDS in Pharmacological Sciences, 2003, vol. 24, pp. 198-205.

Suggs, J. et al., "Facile Synthesis of 8-Substituted Quinolines," J. Org. Chem., 1980, vol. 45, pp. 1514-1515.

Takemori, A. et al., "Selective Natrexone-Derived Opioid Receptor Antagonists," Annu. Rev. Pharmacol. Toxicol., 1992, vol. 32, pp. 239-269.

Vippagunta, S. et al., "Crystalline Solids," Advanced Drug Delivery Reviews, 2001, vol. 48, pp. 3-26.

West, A., "Solid State Chemistry and its Applications," Wiley, New York, 1988, pp. 358 & 365.

Wolff, M., "Burger's Medicinal Chemistry and Drug Discovery, 5ed, Part 1," John Wiley & Sons, 1995, pp. 975-977.

Zhang, X. et al., "Probes for Narcotic Receptor Mediated Phenomena. 26.1-3 Synthesis and Biological Evaluation of Diarylmethylpiperazines and Diarylmethylpiperidines as Novel, Nonpeptidic Delta Opioid Receptor Ligands," J. Med. Chem., 1999, vol. 42, pp. 5455-5463.

International Search Report issued for PCT/SE02/00956 on Sep. 18, 2002.

Non-final Office Action issued for U.S. Appl. No. 10/714,447 on Sep. 10, 2004.

Final Office Action issued for U.S. Appl. No. 10/714,447 on Mar. 22, 2005.

Advisory Action issued for U.S. Appl. No. 10/714,447 on Jul. 5, 2005.

Non-final Office Action issued for U.S. Appl. No. 10/714,447 on Sep. 9, 2005.

Final Office Action issued for U.S. Appl. No. 10/714,447 on Feb. 16, 2006.

Non-final Office Action issued for U.S. Appl. No. 10/477,642 on Jan. 13, 2005.

Non-final Office Action issued for U.S. Appl. No. 10/477,642 on Jun. 15, 2005.

Final Office Action issued for U.S. Appl. No. 10/477,642 on Nov. 25, 2005.

Non-final Office Action issued for U.S. Appl. No. 10/477,642 on Apr. 6, 2006.

Non-final Office Action issued for U.S. Appl. No. 10/533,654 on Apr. 25, 2006.

Non-final Office Action issued for U.S. Appl. No. 10/533,654 on Dec. 1, 2006.

Non-final Office Action issued for U.S. Appl. No. 10/533,764 on Apr. 17, 2006.

Final Office Action issued for U.S. Appl. No. 10/533,764 on Oct. 2, 2006.

Advisory Action issued for U.S. Appl. No. 10/533,764 on Jan. 10, 2007.

Non-final Office Action issued for U.S. Appl. No. 10/533,744 on Jun. 29, 2007.

Final Rejection issued for U.S. Appl. No. 10/533,744 on Dec. 4, 2007.

Non-Final Office Action issued for U.S. Appl. No. 11/243,623 on Dec. 7, 2005.

Final Rejection issued for U.S. Appl. No. 11/243,623 on Jun. 12, 2006.

Non-Final Office Action issued for U.S. Appl. No. 11/243,623 on Aug. 29, 2006.

Final Office Action issued for U.S. Appl. No. 11/243,623 on May 17, 2007.

Non-Final Office Action issued for U.S. Appl. No. 11/243,623 on Sep. 24, 2007.

U.S. Appl. No. 11/816,656, filed Aug. 20, 2007.

English abstract for DE 2431178, Jan. 16, 1975.

English abstract for HU 215847, Apr. 28, 1990.

English abstract for HU 217619, Mar. 28, 2000.

Non-final OA issued for U.S. Appl. No. 11/572,948 on Nov. 16, 2009.
Non-final OA issued for U.S. Appl. No. 11/816,656 on Oct. 28, 2009.
Patani et al., "Bioisosterism: A Rational Approach in Drug Design," 1996, Chem. Rev., vol. 96, pp. 3147-3176.
Non-final OA issued for U.S. Appl. No. 11/243,623 on Jul. 9, 2009.
Examiner's Answer issued for U.S. Appl. No. 11/243,623 on May 27, 2010.
Final Rejection issued for U.S. Appl. No. 11/743,824 on May 14, 2010.
Notice of Allowance issued for U.S. Appl. No. 11/743,824 on Aug. 19, 2010.
Dantzman, "Strategies employed and outcomes of the multi-parameter optimization of 4-piperidin-4-ylidenemethyl-benzamides as potent and selective Delta-Opioid Receptor Agonists" Jun. 14, 2010.
Dantzman et al., "Strategies employed and outcomes of the multi-parameter optimization of 4-piperidin-4-ylidenemethyl-benzamides as potent and selective Delta-Opioid Receptor Agonists" Aug. 25, 2010, 240th ACS National Meeting, Boston, MA.
Dantzman et al., "Strategies employed and outcomes of the multiparameter optimization of 4-piperidin-4-ylidenemethyl-benzamides as potent and selective Delta-Opioid Receptor Agonists" Abstract, (2010).
Griffin et al., "Delta agonist hydroxy bioisosteres: the discovery of 3-((1-benzylpiperidin-4-yl){4-[(diethylamino)carbonyl]phenyl}amino)benzamide with improved delta agonist activity and in vitro metabolic stability" Sep. 22, 2009, Bioorg Med Chem Lett., 19(21):5999-6003.
Jones et al., "N,N-Diethyl-4-[(3-hydroxyphenyl)(piperidin-4-yl)amino] benzamide derivatives: The development of diaryl amino piperidines as potent delta opioid receptor agonists with in vivo anti-nociceptive activity in rodent models," Bioorg. Med. Chem. Lett., 2009, 19 (21), 5994.
Non-final OA issued for U.S. Appl. No. 12/911,167 on Jan. 4, 2011.
U.S. Appl. No. 12/911,167, filed Oct. 25, 2010.

* cited by examiner

`4(PHENYL-PIPERAZINYL-METHYL) BENZAMIDE DERIVATIVES AND THEIR USE FOR THE TREATMENT OF PAIN OR GASTROINTESTINAL DISORDERS`

CROSS-REFERENCE TO RELATED APPLICATIONS

This application is a continuation of U.S. application Ser. No. 10/533,654, now U.S. Pat. No. 7,253,173, filed May 4, 2005, which was the National Stage of International Application No. PCT/SE03/01707, which was filed Nov. 5, 2003, which claims priority under 35 U.S.C 365 and 35 U.S.C. §119 (a)-(d) to Swedish application no. SE 0203303-3, filed Nov. 7, 2002.

BACKGROUND OF THE INVENTION

1. Field of the Invention

The present invention is directed to novel compounds, to a process for their preparation, their use and pharmaceutical compositions comprising the novel compounds. The novel compounds are useful in therapy, and in particular for the treatment of pain, anxiety and functional gastrointestinal disorders.

2. Discussion of Relevant Art

The receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors (μ, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J. et al., Journal of Pharmacology and Experimental Therapeutics, 273(1), pp. 359-366 (1995)).

Many δ agonist compounds that have been identified in the prior art have many disadvantages in that they suffer from poor pharmacokinetics and are not analgesic when administered by systemic routes. Also, it has been documented that many of these δ agonist compounds show significant convulsive effects when administered systemically.

U.S. Pat. No. 6,130,222 to Roberts et al. describes some δ-agonists.

However, there is still a need for improved δ-agonists.

DESCRIPTION OF THE INVENTION

Definitions

Unless specified otherwise within this specification, the nomenclature used in this specification generally follows the examples and rules stated in *Nomenclature of Organic Chemistry, Sections A, B, C, D, E, F, and H*, Pergamon Press, Oxford, 1979, which is incorporated by references herein for its exemplary chemical structure names and rules on naming chemical structures.

The term "$C_{m-n}$" or "$C_{m-n}$ group" used alone or as a prefix, refers to any group having m to n carbon atoms.

The term "hydrocarbon" used alone or as a suffix or prefix, refers to any structure comprising only carbon and hydrogen atoms up to 14 carbon atoms.

The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms.

The term "alkylene" used alone or as suffix or prefix, refers to divalent straight or branched chain hydrocarbon radicals comprising 1 to about 12 carbon atoms, which serves to links two structures together.

The term "alkenyl" used alone or as suffix or prefix, refers to a monovalent straight or branched chain hydrocarbon radical having at least one carbon-carbon double bond and comprising at least 2 up to about 12 carbon atoms.

The term "alkynyl" used alone or as suffix or prefix, refers to a monovalent straight or branched chain hydrocarbon radical having at least one carbon-carbon triple bond and comprising at least 2 up to about 12 carbon atoms.

The term "cycloalkyl," used alone or as suffix or prefix, refers to a monovalent ring-containing hydrocarbon radical comprising at least 3 up to about 12 carbon atoms.

The term "cycloalkenyl" used alone or as suffix or prefix, refers to a monovalent ring-containing hydrocarbon radical having at least one carbon-carbon double bond and comprising at least 3 up to about 12 carbon atoms.

The term "cycloalkynyl" used alone or as suffix or prefix, refers to a monovalent ring-containing hydrocarbon radical having at least one carbon-carbon triple bond and comprising about 7 up to about 12 carbon atoms.

The term "aryl" used alone or as suffix or prefix, refers to a monovalent hydrocarbon radical having one or more polyunsaturated carbon rings having aromatic character, (e.g. 4 n+2 delocalized electrons) and comprising 5 up to about 14 carbon atoms.

The term "arylene" used alone or as suffix or prefix, refers to a divalent hydrocarbon radical having one or more polyunsaturated carbon rings having aromatic character, (e.g. 4 n+2 delocalized electrons) and comprising 5 up to about 14 carbon atoms, which serves to link two structures together.

The term "heterocycle" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroaromatic" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4 n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen therefrom.

The term "heterocyclylene" used alone or as a suffix or prefix, refers to a divalent radical derived from a heterocycle by removing two hydrogens therefrom, which serves to links two structures together.

The term "heteroaryl" used alone or as a suffix or prefix, refers to a heterocyclyl having aromatic character.

The term "heterocylcoalkyl" used alone or as a suffix or prefix, refers to a heterocyclyl that does not have aromatic character.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as prefix refers to a group having a ring that contains six ring atoms.

The term "five-membered" used as prefix refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "substituted" used as a prefix refers to a structure, molecule or group, wherein one or more hydrogens are replaced with one or more $C_{1-6}$ hydrocarbon groups, or one or more chemical groups containing one or more heteroatoms selected from N, O, S, F, Cl, Br, I, and P. Exemplary chemical groups containing one or more heteroatoms include —$NO_2$, —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, —NRC(=O)R, oxo (=O), imino (=NR), thio (=S), and oximino (=N—OR), wherein each "R" is a $C_{1-6}$ hydrocarbyl. For example, substituted phenyl may refer to nitrophenyl, methoxyphenyl, chlorophenyl, aminophenyl, etc., wherein the nitro, methoxy, chloro, and amino groups may replace any suitable hydrogen on the phenyl ring.

The term "substituted" used as a suffix of a first structure, molecule or group, followed by one or more names of chemical groups refers to a second structure, molecule or group, which is a result of replacing one or more hydrogens of the first structure, molecule or group with the one or more named chemical groups. For example, a "phenyl substituted by nitro" refers to nitrophenyl.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy" used alone or as a suffix or prefix, refers to radicals of the general formula —O—R, wherein R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

The term "amine" or "amino" used alone or as a suffix or prefix, refers to radicals of the general formula —NRR', wherein R and R' are independently selected from hydrogen or a hydrocarbon radical.

Halogen includes fluorine, chlorine, bromine and iodine.

"Halogenated," used as a prefix of a group, means one or more hydrogens on the group is replaced with one or more halogens.

"RT" or "rt" means room temperature.

DESCRIPTION OF EMBODIMENTS

In one aspect, the invention provides a compound of formula I, a pharmaceutically acceptable salt thereof, diastereomers thereof, enantiomers thereof, and mixtures thereof:

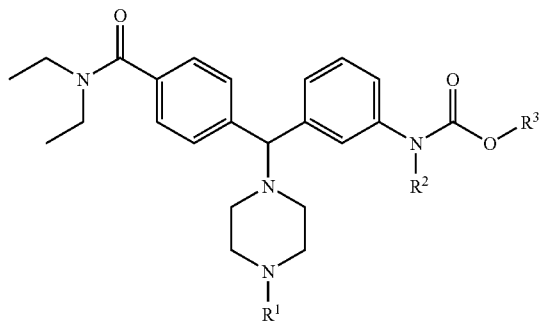

I wherein $R^1$ is selected from —H, $C_{6-10}$aryl, $C_{2-6}$heteroaryl, $C_{6-10}$aryl-$C_{1-4}$alkyl, and $C_{2-6}$heteroaryl-$C_{1-4}$alkyl, wherein said $C_{6-10}$aryl, $C_{2-6}$heteroaryl, $C_{6-10}$aryl-$C_{1-4}$alkyl, and $C_{2-6}$heteroaryl-$C_{1-4}$alkyl are optionally substituted with one or more groups selected from —R, —$NO_2$, —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, —NRC(=O)R, and —NRC(=O)—OR, wherein R is, independently, a hydrogen or $C_{1-6}$alkyl;

$R^2$ is selected from —H, $C_{1-6}$alkyl and $C_{3-6}$cycloalkyl, wherein said $C_{1-6}$alkyl and $C_{3-6}$cycloalkyl are optionally substituted with one or more groups selected from —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, —NRC(=O)R, and —NRC(=O)—OR, wherein R is, independently, a hydrogen or $C_{1-6}$alkyl; and $R^3$ is selected from $C_{1-6}$alkyl and $C_{3-6}$cycloalkyl, wherein said $C_{1-6}$alkyl and $C_{3-6}$cycloalkyl are optionally substituted with one or more groups selected from —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, —NRC(=O)R, and —NRC(=O)—OR, wherein R is, independently, a hydrogen or $C_{1-6}$alkyl.

In another embodiment, the compounds of the present invention are those of formula I, wherein $R^1$ is —$CH_2$—$R^4$, wherein $R^4$ is selected from phenyl; pyridyl; thienyl; furyl; imidazolyl; triazolyl; pyrrolyl; thiazolyl; and N-oxido-pyridyl, wherein said phenyl; pyridyl; thienyl; furyl; imidazolyl; triazolyl; pyrrolyl; thiazolyl; and N-oxido-pyridyl are optionally substituted with one or more groups selected from $C_{1-6}$alkyl, halogenated $C_{1-6}$alkyl, —$NO_2$, —$CF_3$, $C_{1-6}$ alkoxy, chloro, fluoro, bromo, and iodo;

$R^2$ is selected from —H and $C_{1-3}$alkyl; and $R^3$ is selected from $C_{1-6}$alkyl, and $C_{3-6}$cycloalkyl.

In another embodiment, the compounds of the present invention are those of formula I, wherein $R^1$ is —$CH_2$—$R^4$, wherein $R^4$ is selected from phenyl; pyridyl; thienyl; furyl; imidazolyl; pyrrolyl and thiazolyl;

$R^2$ is selected from —H and methyl; and $R^3$ is selected from methyl, ethyl, propyl and isopropyl.

In a further embodiment, the compounds of the present invention are those of formula I, wherein $R^1$ is —H;

$R^2$ is selected from —H and $C_{1-3}$alkyl; and $R^3$ is selected from $C_{1-6}$alkyl, and $C_{3-6}$cycloalkyl.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the formula I.

It will also be understood that certain compounds of the present invention may exist in solvated, for example hydrated, as well as unsolvated forms. It will further be understood that the present invention encompasses all such solvated forms of the compounds of the formula I.

Within the scope of the invention are also salts of the compounds of the formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate orp-toluenesulphonate.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhea, depression, anxiety and stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following myocardial infarction, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anesthetics, hypnotics, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

Thus, the invention provides a compound of formula I, or pharmaceutically acceptable salt or solvate thereof, as hereinbefore defined for use in therapy.

In a further aspect, the present invention provides the use of a compound of formula I, or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be contrued accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: chronic pain, neuropathic pain, acute pain, back pain, cancer pain, and visceral pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be orally, intravenously or intramuscularly.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid and liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of formula I as defined above for the manufacture of a medicament.

Also within the scope of the invention is the use of any compound of formula I for the manufacture of a medicament for the therapy of pain.

Additionally provided is the use of any compound according to Formula I for the manufacture of a medicament for the therapy of various pain conditions including, but not limited to: chronic pain, neuropathic pain, acute pain, back pain, cancer pain, and visceral pain.

A further aspect of the invention is a method for therapy of a subject suffering from any of the conditions discussed above, whereby an effective amount of a compound according to the formula I above, is administered to a patient in need of such therapy.

Additionally, there is provided a pharmaceutical composition comprising a compound of Formula I, or a pharmaceutically acceptable salt thereof, in association with a pharmaceutically acceptable carrier.

Particularly, there is provided a pharmaceutical composition comprising a compound of Formula I, or a pharmaceutically acceptable salt thereof, in association with a pharmaceutically acceptable carrier for therapy, more particularly for therapy of pain.

Further, there is provided a pharmaceutical composition comprising a compound of Formula I, or a pharmaceutically acceptable salt thereof, in association with a pharmaceutically acceptable carrier use in any of the conditions discussed above.

In a further aspect, the present invention provides a method of preparing a compound of formula I.

In one embodiment, the invention provides a process for preparing a compound of formula II, comprising:

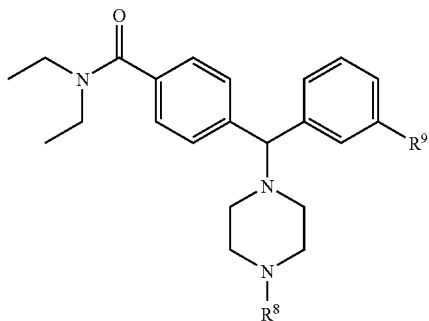

a) reacting a compound of formula III:

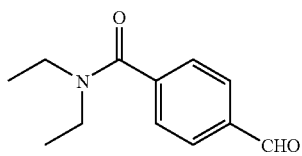

with a compound of formula IV

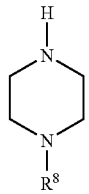

in the presence of benzotriazole; and
b) reacting a product formed in step a) with a compound of formula V to form the compound of formula II,

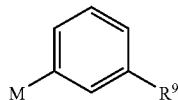

wherein
$R^8$ is selected from $C_{1-6}$alkyl-O—C(=O)—, $C_{6-10}$aryl-$C_{1-4}$alkyl, and $C_{2-6}$heteroaryl-$C_{1-4}$alkyl, wherein said $C_{1-6}$alkyl-O—C(=O)—, $C_{6-10}$aryl-$C_{1-4}$alkyl, and $C_{2-6}$heteroaryl-$C_{1-4}$alkyl are optionally substituted with one or more groups selected from $C_{1-6}$alkyl, halogenated $C_{1-6}$alkyl, —$NO_2$, —$CF_3$, $C_{1-6}$ alkoxy, chloro, fluoro, bromo, and iodo;
M is selected from Li, Na, K, —$ZnX^1$, and —$MgX^1$, wherein $X^1$ is a halogen; and
$R^9$ is selected from hydrogen, —R, —$NO_2$, —OR, —Cl, —Br, —I, —F, —$CF_3$, —C(=O)R, —C(=O)OH, —$NH_2$, —SH, —NHR, —$NR_2$, —SR, —$SO_3H$, —$SO_2R$, —S(=O)R, —CN, —OH, —C(=O)OR, —C(=O)$NR_2$, —NRC(=O)R, and —NRC(=O)—OR, wherein R is, independently, a hydrogen or $C_{1-6}$hydrocarbyl.

In another embodiment, the invention provides a process for preparing a compound of formula VII:

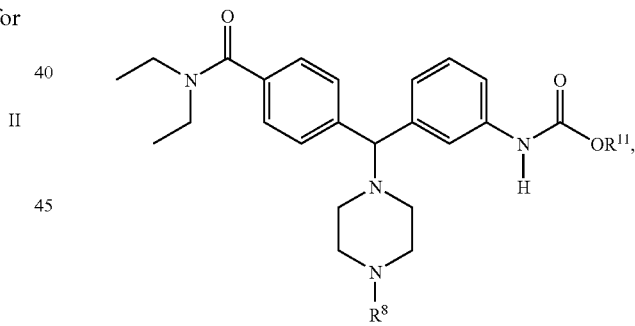

comprising:
reacting a compound of formula VIII

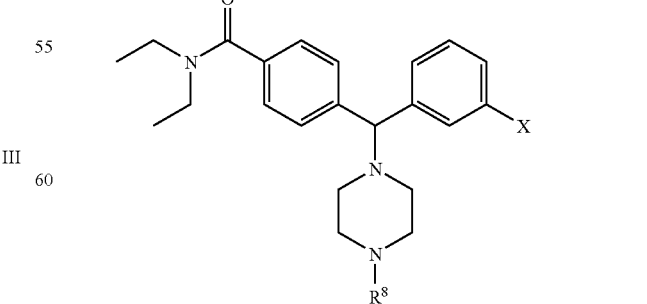

with a $C_{1-6}$alkylcarbamate to form the compound of formula VII, wherein
R[8] is selected from $C_{1-6}$alkyl-O—C(=O)—, $C_{6-10}$aryl-$C_{1-4}$alkyl, and $C_{2-6}$heteroaryl-$C_{1-4}$alkyl, wherein said $C_{1-6}$alkyl-O—C(=O)—, $C_{6-10}$aryl-$C_{1-4}$alkyl, and $C_{2-6}$heteroaryl-$C_{1-4}$alkyl are optionally substituted with one or more groups selected from —OR, —Cl, —Br, —I, —F, —CF$_3$, —C(=O)R, —C(=O)OH, —NH$_2$, —SH, —NHR, —NR$_2$, —SR, —SO$_3$H, —SO$_2$R, —S(=O)R, —CN, —OH, —C(=O)OR, —C(=O)NR$_2$, —NRC(=O)R, and —NRC(=O)—OR, wherein R is, independently, a hydrogen or $C_{1-6}$alkyl;

X is selected from halogen, triflate, and sulfonamide; and R[11] is a $C_{1-6}$alkyl.

In a further embodiment, the invention provides a process for preparing a compound of formula X,

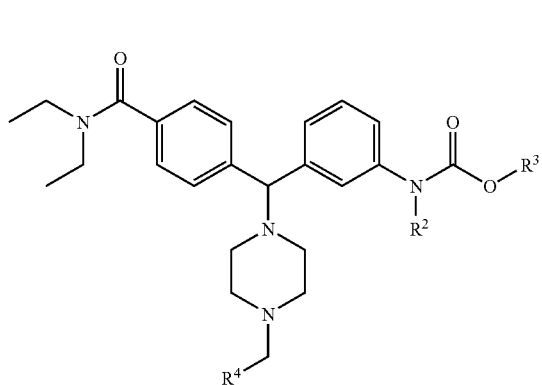

X comprising:
reacting a compound of formula IX,

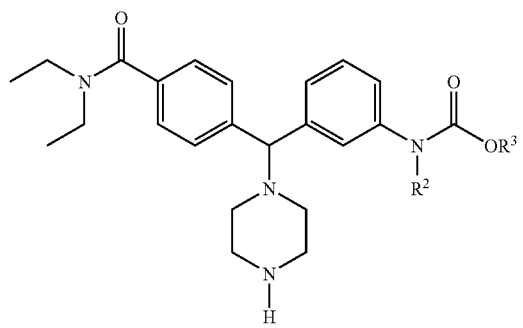

IX with R[4]—CHO to form the compound of formula X, wherein

R[4] is selected from phenyl; pyridyl; thienyl; furyl; imidazolyl; triazolyl; pyrrolyl; thiazolyl; and N-oxido-pyridyl, wherein said phenyl; pyridyl; thienyl; furyl; imidazolyl; triazolyl; pyrrolyl; thiazolyl; and N-oxido-pyridyl are optionally substituted with one or more groups selected from $C_{1-6}$alkyl, halogenated $C_{1-6}$alkyl, —NO$_2$, —CF$_3$, $C_{1-6}$ alkoxy, chloro, fluoro, bromo, and iodo;

R[2] is selected from —H, $C_{1-6}$alkyl and $C_{3-6}$cycloalkyl, wherein said $C_{1-6}$alkyl and $C_{3-6}$cycloalkyl are optionally substituted with one or more groups selected from —OR, —Cl, —Br, —I, —F, —CF$_3$, —C(=O)R, —C(=O)OH, —NH$_2$, —SH, —NHR, —NR$_2$, —SR, —SO$_3$H, —SO$_2$R, —S(=O)R, —CN, —OH, —C(=O)OR, —C(=O)NR$_2$, —NRC(=O)R, and —NRC(=O)—OR, wherein R is, independently, a hydrogen or $C_{1-6}$alkyl; and R[3] is selected from $C_{1-6}$alkyl and $C_{3-6}$cycloalkyl, wherein said $C_{1-6}$alkyl and $C_{3-6}$cycloalkyl are optionally substituted with one or more groups selected from —OR, —Cl, —Br, —I, —F, —CF$_3$, —C(=O)R, —C(=O)OH, —NH$_2$, —SH, —NHR, —NR$_2$, —SR, —SO$_3$H, —SO$_2$R, —S(=O)R, —CN, —OH, —C(=O)OR, —C(=O)NR$_2$, —NRC(=O)R, and —NRC(=O)—OR, wherein R is, independently, a hydrogen or $C_{1-6}$alkyl.

Particularly, the compounds of the present invention can be prepared according to the synthetic routes as exemplified in Schemes 1-7.

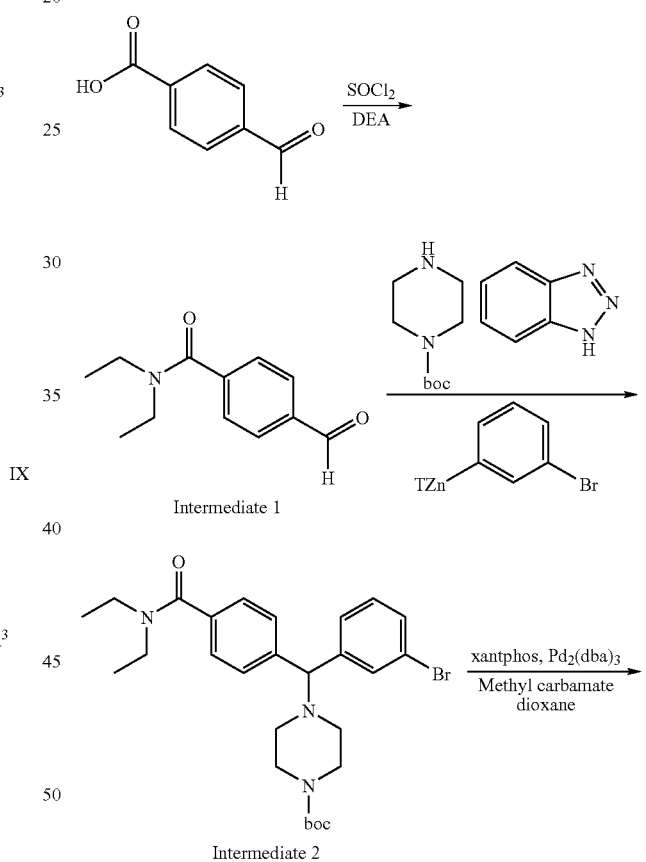

Scheme 1

Intermediate 1

Intermediate 2

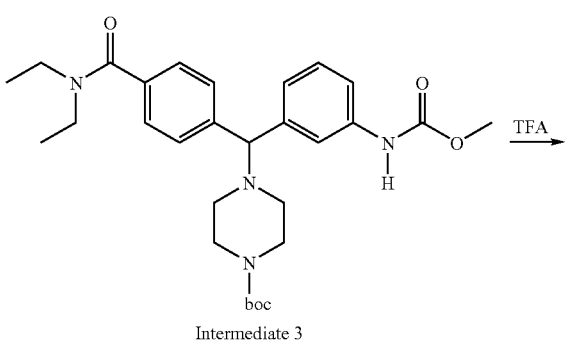

Intermediate 3

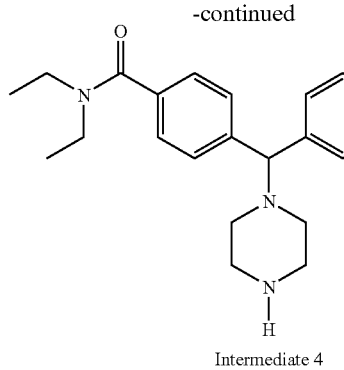
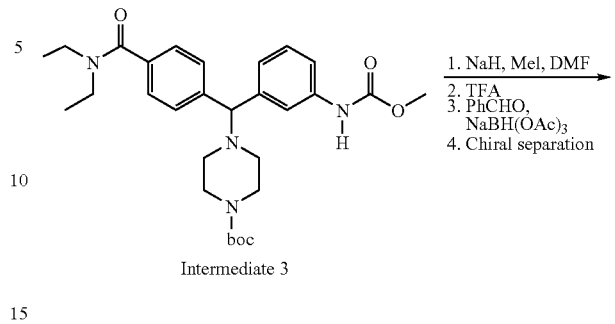
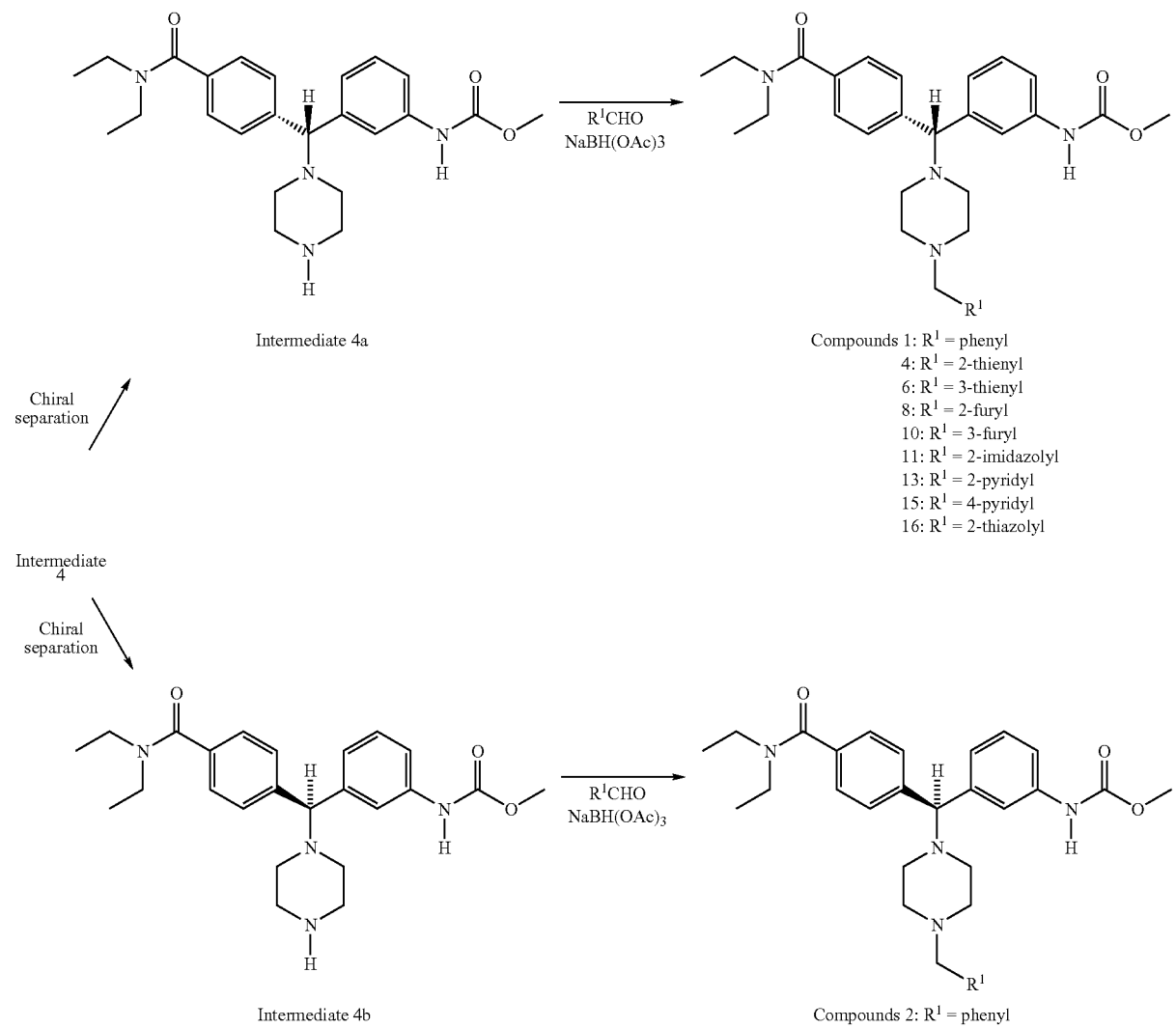

15
-continued
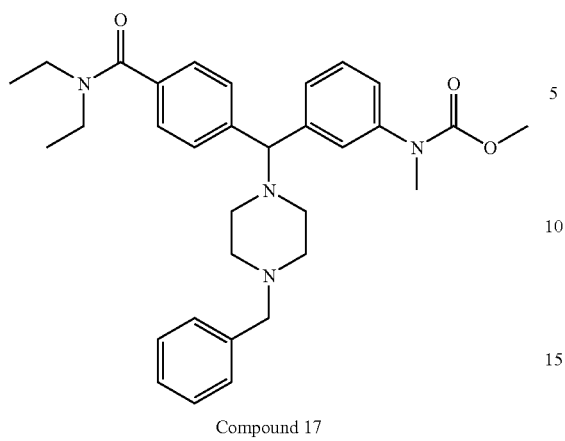
Compound 17
Scheme 4
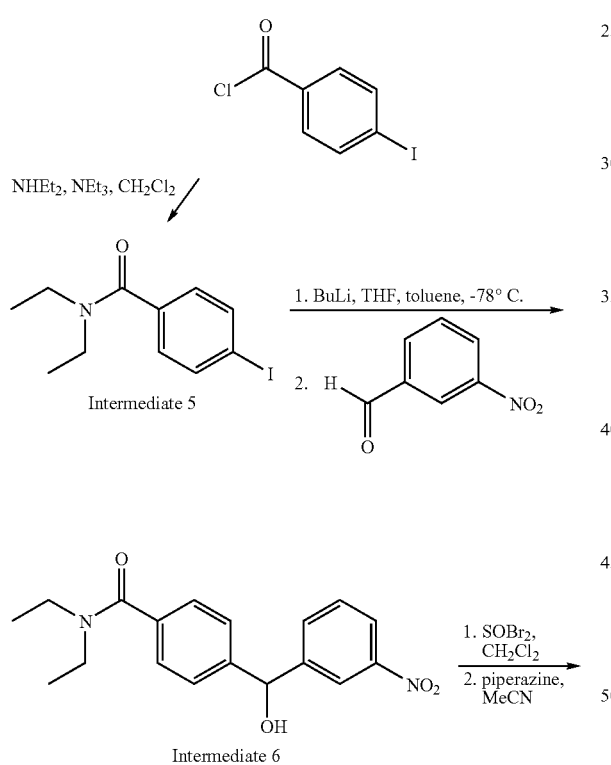
16
-continued
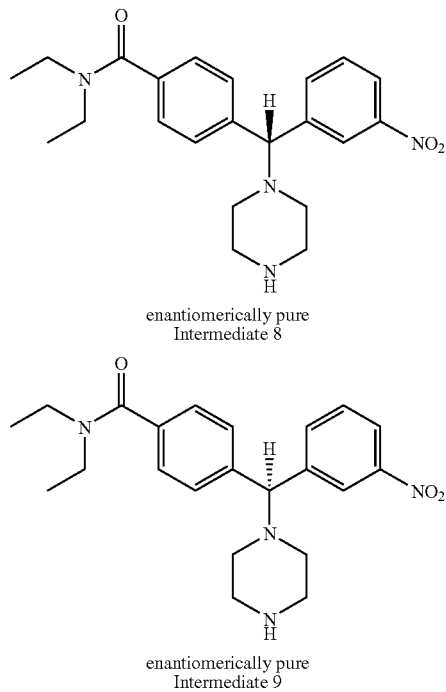
Scheme 5
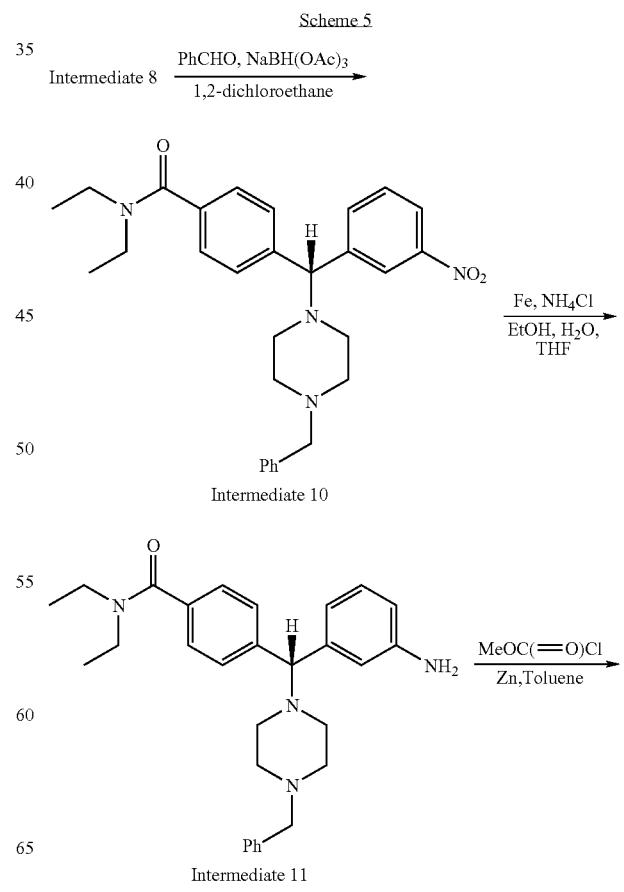

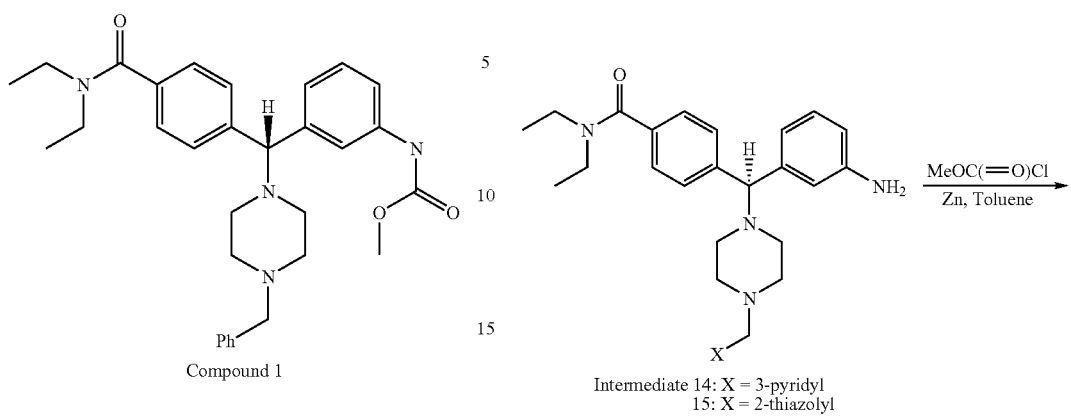
Compound 1
Intermediate 14: X = 3-pyridyl
15: X = 2-thiazolyl
Scheme 6
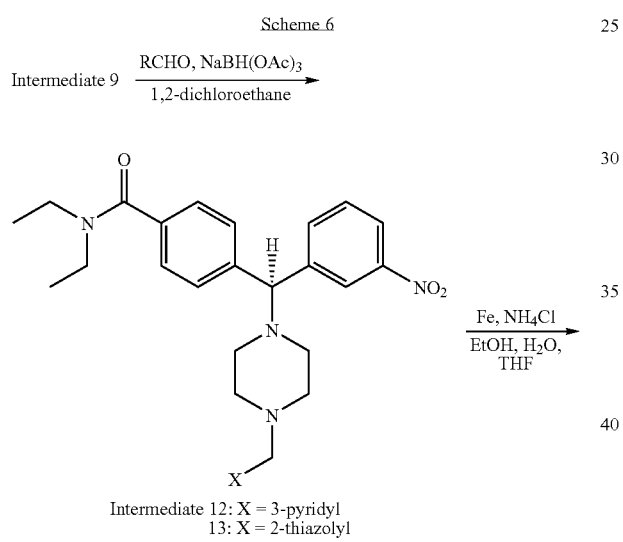
Intermediate 12: X = 3-pyridyl
13: X = 2-thiazolyl
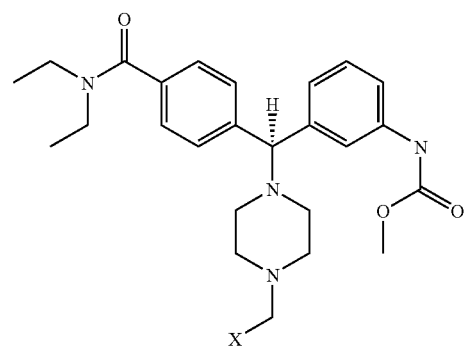
Compounds 18: X = 3-pyridyl
19: X = 2-thiazolyl
Scheme 7
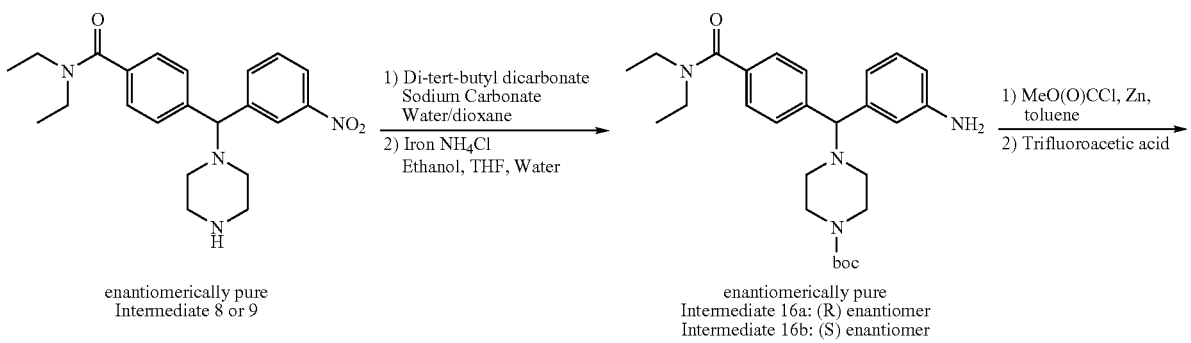
enantiomerically pure
Intermediate 8 or 9
enantiomerically pure
Intermediate 16a: (R) enantiomer
Intermediate 16b: (S) enantiomer

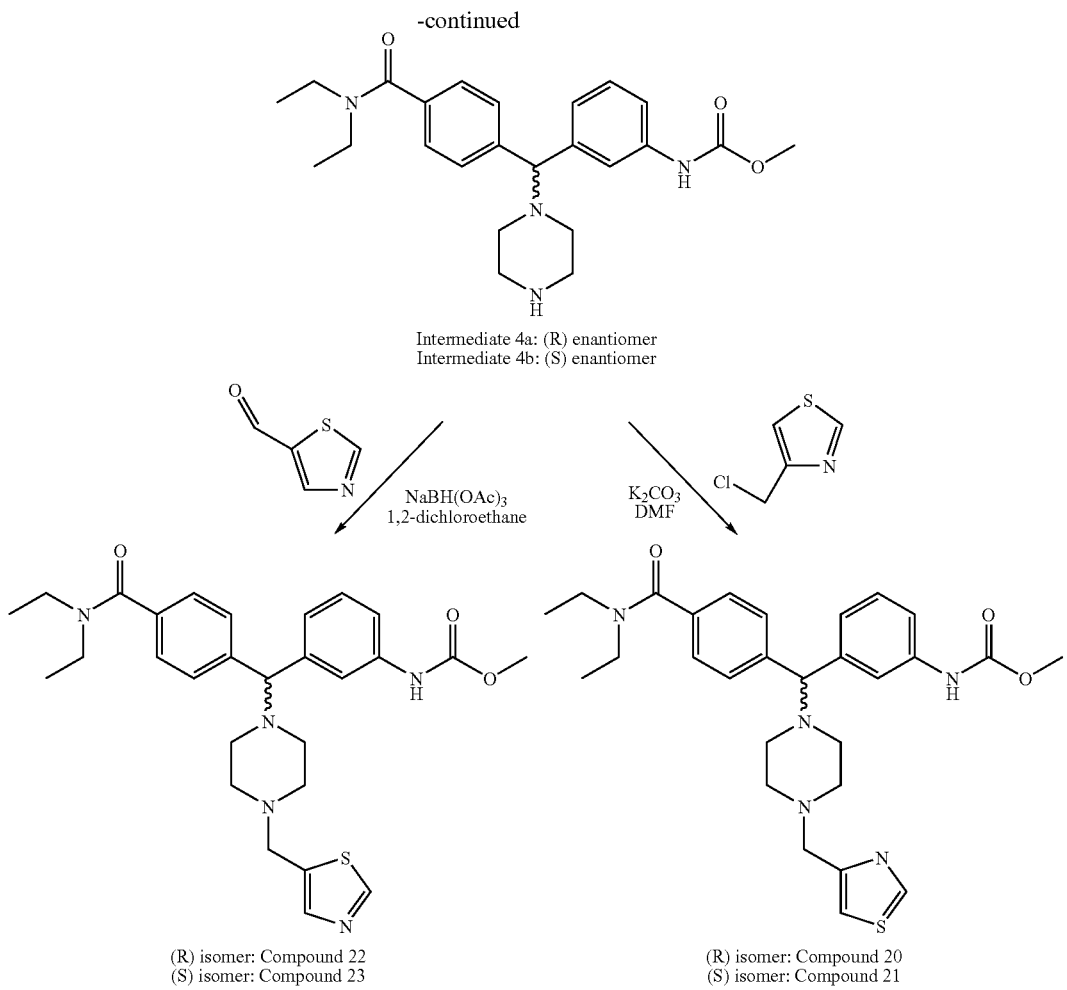

Accordingly, a further aspect of the invention is a compound of formula XI, a pharmaceutically acceptable salt thereof, diastereomers, enantiomers, or mixtures thereof:

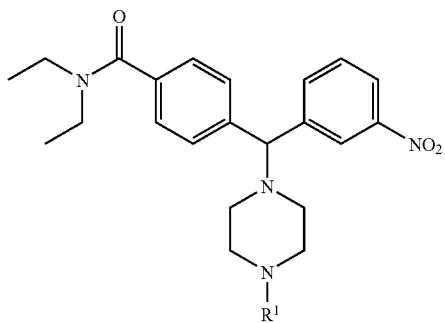

XI wherein

R¹ is selected from —H, $C_{6-10}$aryl, $C_{2-6}$heteroaryl, $C_{6-10}$aryl-$C_{1-4}$alkyl, and $C_{2-6}$heteroaryl-$C_{1-4}$alkyl, wherein said $C_{6-10}$aryl, $C_{2-6}$heteroaryl, $C_{6-10}$aryl-$C_{1-4}$alkyl, and $C_{2-6}$heteroaryl-$C_{1-4}$alkyl are optionally substituted with one or more groups selected from —R, —NO₂, —OR, —Cl, —Br, —I, —F, —CF₃, —C(=O)R, —C(=O)OH, —NH₂, —SH, —NHR, —NR₂, —SR, —SO₃H, —SO₂R, —S(=O)R, —CN, —OH, —C(=O)OR, —C(=O)NR₂, —NRC(=O)R, and —NRC(=O)—OR, wherein R is, independently, a hydrogen or $C_{1-6}$alkyl.

Biological Evaluation

The compounds of the invention are found to be active towards δ receptors in warm-blooded animal, e.g., human. Particularly the compounds of the invention are found to be effective δ receptor ligands. In vitro assays, infra, demonstrate these surprising activities, especially with regard to agonists potency and efficacy as demonstrated in the rat brain functional assay and/or the human δ receptor functional assay (low). This feature may be related to in vivo activity and may not be linearly correlated with binding affinity. In these in vitro assays, a compound is tested for their activity toward δ receptors and $IC_{50}$ is obtained to determine the selective activity for a particular compound towards δ receptors. In the current context, $IC_{50}$ generally refers to the concentration of the compound at which 50% displacement of a standard radioactive δ receptor ligand has been observed.

The activities of the compound towards κ and μ receptors are also measured in a similar assay.

In Vitro Model

Cell Culture

A. Human 293S cells expressing cloned human κ, δ and μ receptors and neomycin resistance are grown in suspension at 37° C. and 5% CO₂ in shaker flasks containing calcium-free DMEM10% FBS, 5% BCS, 0.1% Pluronic F-68, and 600 μg/ml geneticin.

B. Rat brains are weighed and rinsed in ice-cold PBS (containing 2.5 mM EDTA, pH 7.4). The brains are homogenized with a polytron for 30 sec (rat) in ice-cold lysis buffer (50 mM Tris, pH 7.0, 2.5 mM EDTA, with phenylmethylsulfonyl fluoride added just prior use to 0.5 MmM from a 0.5M stock in DMSO:ethanol).

Membrane Preparation

Cells are pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension is spun at 1000 g (max) for 10 min at 4° C. The supernatant is saved on ice and the pellets resuspended and spun as before. The supernatants from both spins are combined and spun at 46,000 g(max) for 30 min. The pellets are resuspended in cold Tris buffer (50 mM Tris/Cl, pH 7.0) and spun again. The final pellets are resuspended in membrane buffer (50 mM Tris, 0.32 M sucrose, pH 7.0). Aliquots (1 ml) in polypropylene tubes are frozen in dry ice/ethanol and stored at −70° C. until use. The protein concentrations are determined by a modified Lowry assay with sodium dodecyl sulfate.

Binding Assays

Membranes are thawed at 37° C., cooled on ice, passed 3 times through a 25-gauge needle, and diluted into binding buffer (50 mM Tris, 3 mM $MgCl_2$, 1 mg/ml BSA (Sigma A-7888), pH 7.4, which is stored at 4° C. after filtration through a 0.22 m filter, and to which has been freshly added 5 μg/ml aprotinin, 10 μM bestatin, 10 μM diprotin A, no DTT). Aliquots of 100 μl are added to iced 12×75 mm polypropylene tubes containing 100 μl of the appropriate radioligand and 100 μl of test compound at various concentrations. Total (TB) and nonspecific (NS) binding are determined in the absence and presence of 10 μM naloxone respectively. The tubes are vortexed and incubated at 25° C. for 60-75 min, after which time the contents are rapidly vacuum-filtered and washed with about 12 ml/tube iced wash buffer (50 mM Tris, pH 7.0, 3 mM $MgCl_2$) through GF/B filters (Whatman) presoaked for at least 2 h in 0.1% polyethyleneimine. The radioactivity (dpm) retained on the filters is measured with a beta counter after soaking the filters for at least 12 h in minivials containing 6-7 ml scintillation fluid. If the assay is set up in 96-place deep well plates, the filtration is over 96-place PEI-soaked unifilters, which are washed with 3×1 ml wash buffer, and dried in an oven at 55° C. for 2 h. The filter plates are counted in a TopCount (Packard) after adding 50 μl MS-20 scintillation fluid/well.

Functional Assays

The agonist activity of the compounds is measured by determining the degree to which the compounds receptor complex activates the binding of GTP to G-proteins to which the receptors are coupled. In the GTP binding assay, $GTP[\gamma]^{35}S$ is combined with test compounds and membranes from HEK-293S cells expressing the cloned human opioid receptors or from homogenised rat and mouse brain. Agonists stimulate $GTP[\gamma]^{35}S$ binding in these membranes. The $EC_{50}$ and $E_{max}$ values of compounds are determined from dose-response curves. Right shifts of the dose response curve by the delta antagonist naltrindole are performed to verify that agonist activity is mediated through delta receptors. For human δ receptor functional assays, $EC_{50}$ (low) is measured when the human δ receptors used in the assay were expressed at lower levels in comparison with those used in determining $EC_{50}$ (high). The $E_{max}$ values were determined in relation to the standard δ agonist SNC80, i.e., higher than 100% is a compound that have better efficacy than SNC80.

Procedure for Rat Brain GTP

Rat brain membranes are thawed at 37° C., passed 3 times through a 25-gauge blunt-end needle and diluted in the GTPγS binding (50 mM Hepes, 20 mM NaOH, 100 mM NaCl, 1 mM EDTA, 5 mM $MgCl_2$, pH 7.4, Add fresh: 1 mM DTT, 0.1% BSA). 120 μM GDP final is added membranes dilutions. The EC50 and Emax of compounds are evaluated from 10-point dose-response curves done in 300 μl with the appropriate amount of membrane protein (20 μg/well) and 100000-130000 dpm of $GTP\gamma^{35}S$ per well (0.11-0.14 nM). The basal and maximal stimulated binding are determined in absence and presence of 3 μM SNC-80

Data Analysis

The specific binding (SB) was calculated as TB-NS, and the SB in the presence of various test compounds was expressed as percentage of control SB. Values of $IC_{50}$ and Hill coefficient ($n_H$) for ligands in displacing specifically bound radioligand were calculated from logit plots or curve fitting programs such as Ligand, GraphPad Prism, SigmaPlot, or ReceptorFit. Values of $K_i$ were calculated from the Cheng-Prussoff equation. Mean ±S.E.M. values of $IC_{50}$, $K_i$ and $n_H$ were reported for ligands tested in at least three displacement curves.

Based on the above testing protocols, we find that the compounds of the present invention and some of the intermediates used in the preparation thereof are active toward human δ receptors. Biological activity of the compounds and selected intermediates of the present invention is indicated in Tables 1 and 2.

TABLE 1

| Compd. # | Human δ (nM) | | | Human κ $IC_{50}$ | Human μ $IC_{50}$ | RAT BRAIN (nM) | |
|---|---|---|---|---|---|---|---|
| | $IC_{50}$ | $EC_{50}$ (high) | % EMax (high) | | | $EC_{50}$ | % EMax |
| 1-11 | 0.25-0.74 | 0.55-1.93 | 89-102 | 247-1636 | 93-1100 | 0.93-16.7 | 135-170 |

TABLE 2

| Compd. # | Human δ (nM) | | | Human κ (low) $IC_{50}$ | Human μ $IC_{50}$ |
|---|---|---|---|---|---|
| | $IC_{50}$ | $EC_{50}$ (low) | % EMax (low) | | |
| 12-23, and Interm. 4a | 0.18-4.18 | 3.26-484 | 58-106 | 1277-8728 | 92-6560 |

Receptor Saturation Experiments

Radioligand $K_\delta$ values are determined by performing the binding assays on cell membranes with the appropriate radioligands at concentrations ranging from 0.2 to 5 times the estimated $K_\delta$ (up to 10 times if amounts of radioligand required are feasible). The specific radioligand binding is expressed as pmole/mg membrane protein. Values of $K_\delta$ and $B_{max}$ from individual experiments are obtained from nonlinear fits of specifically bound (B) vs. nM free (F) radioligand from individual according to a one-site model.

Determination of Mechano-Allodynia Using Von Frey Testing

Testing is performed between 08:00 and 16:00 h using the method described by Chaplan et al. (1994). Rats are placed in Plexiglas cages on top of a wire mesh bottom which allows access to the paw, and are left to habituate for 10-15 min. The area tested is the mid-plantar left hind paw, avoiding the less sensitive foot pads. The paw is touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair is applied from underneath the mesh floor perpendicular to the plantar surface with sufficient force to cause a slight buckling against the paw, and held for approximately 6-8 seconds. A positive response is noted if the paw is sharply withdrawn. Flinching immediately upon removal of the hair is also considered a positive response. Ambulation is considered an ambiguous response, and in such cases the stimulus is repeated.

Testing Protocol

The animals are tested on postoperative day 1 for the FCA-treated group. The 50% withdrawal threshold is determined using the up-down method of Dixon (1980). Testing is started with the 2.04 g hair, in the middle of the series. Stimuli are always presented in a consecutive way, whether ascending or descending. In the absence of a paw withdrawal response to the initially selected hair, a stronger stimulus is presented; in the event of paw withdrawal, the next weaker stimulus is chosen. Optimal threshold calculation by this method requires 6 responses in the immediate vicinity of the 50% threshold, and counting of these 6 responses begins when the first change in response occurs, e.g. the threshold is first crossed. In cases where thresholds fall outside the range of stimuli, values of 15.14 (normal sensitivity) or 0.41 (maximally allodynic) are respectively assigned. The resulting pattern of positive and negative responses is tabulated using the convention, X=no withdrawal; O=withdrawal, and the 50% withdrawal threshold is interpolated using the formula:

$$50\% \text{ g threshold} = 10^{(Xf+k\delta)}/10{,}000$$

where Xf=value of the last von Frey hair used (log units); k=tabular value (from Chaplan et al. (1994)) for the pattern of positive/negative responses; and $\delta$=mean difference between stimuli (log units). Here $\delta$=0.224.

Von Frey thresholds are converted to percent of maximum possible effect (% MPE), according to Chaplan et al. 1994. The following equation is used to compute % MPE:

$$\% \text{ MPE} = \frac{\text{Drug treated threshold (g)} - \text{allodynia threshold (g)}}{\text{Control threshold (g)} - \text{allodynia threshold (g)}} \times 100$$

Administration of Test Substance

Rats are injected (subcutaneously, intraperitoneally, intravenously or orally) with a test substance prior to von Frey testing, the time between administration of test compound and the von Frey test varies depending upon the nature of the test compound.

Writhing Test

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflex is considered only when the following elements are present: the animal is not in movement; the lower back is slightly depressed; the plantar aspect of both paws is observable. In this assay, compounds of the present invention demonstrate significant inhibition of writhing responses after oral dosing of 1-100 µmol/kg.

(i) Solutions Preparation

Acetic acid (AcOH): 120 µL of Acetic Acid is added to 19.88 ml of distilled water in order to obtain a final volume of 20 ml with a final concentration of 0.6% AcOH. The solution is then mixed (vortex) and ready for injection.

Compound (drug): Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 µL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

For the anxiety and anxiety-like indications, efficacy has been established in the geller-seifter conflict test in the rat.

For the functional gastrointestina disorder indication, efficacy can be established in the assay described by Coutinho S V et al., in American Journal of Physiology—Gastrointestinal & Liver Physiology. 282(2):G307-16, 2002 February, in the rat.

Additional In Vivo Testing Protocols

Subjects and Housing

Naïve male Sprague Dawley rats (175-200 g) are housed in groups of 5 in a temperature controlled room (22° C., 40-70% humidity, 12-h light/dark). Experiments are performed during the light phase of the cycle. Animals have food and water ad libitum and are sacrificed immediately after data acquisition.

Sample

Compound (Drug) testing includes groups of rats that do not receive any treatment and others that are treated with *E. coli* lipopolysaccharide(LPS). For the LPS-treated experiment, four groups are injected with LPS, one of the four groups is then vehicle-treated whilst the other three groups are injected with the drug and its vehicle. A second set of experiments are conducted involving five groups of rats; all of which receive no LPS treatment. The naïve group receives no compound (drug) or vehicle; the other four groups are treated with vehicle with or without drug. These are performed to determine anxiolytic or sedative effects of drugs which can contribute to a reduction in USV.

Administration of LPS

Rats are allowed to habituate in the experimental laboratory for 15-20 min prior to treatment. Inflammation is induced by administration of LPS (endotoxin of gram-negative *E. coli* bacteria serotype 0111:B4, Sigma). LPS (2.4 µg) is injected intracerebro-ventricularly (i.c.v.), in a volume of 10 µl, using standard stereotaxic surgical techniques under isoflurane anaesthesia. The skin between the ears is pushed rostrally and a longitudinal incision of about 1 cm is made to expose the skull surface. The puncture site is determined by the coordinates: 0.8 mm posterior to the bregma, 1.5 mm lateral (left) to the lambda (sagittal suture), and 5 mm below the surface of the skull (vertical) in the lateral ventricle. LPS is injected via a sterile stainless steel needle (26-G ⅜) of 5 mm long attached to a 100-µl Hamilton syringe by polyethylene tubing (PE20; 10-15 cm). A 4 mm stopper made from a cut needle (20-G) is placed over and secured to the 26-G needle by silicone glue to create the desired 5 mm depth.

Following the injection of LPS, the needle remains in place for an additional 10 s to allow diffusion of the compound, then is removed. The incision is closed, and the rat is returned to its original cage and allowed to rest for a minimum of 3.5 h prior to testing.

Experimental Setup for Air-puff Stimulation

The rats remains in the experimental laboratory following LPS injection and compound (drug) administration. At the time of testing all rats are removed and placed outside the laboratory. One rat at a time is brought into the testing laboratory and placed in a clear box (9×9×18 cm) which is then placed in a sound-attenuating ventilated cubicle measuring 62(w)×35(d)×46(h) cm (BRS/LVE, Div. Tech-Serv Inc). The delivery of air-puffs, through an air output nozzle of 0.32 cm, is controlled by a system (AirStim, San Diego Intruments) capable of delivering puffs of air of fixed duration (0.2 s) and fixed intensity with a frequency of 1 puff per 10 s. A maximum of 10 puffs are administered, or until vocalisation starts, which ever comes first. The first air puff marks the start of recording.

Experimental Setup for and Ultrasound Recording

The vocalisations are recorded for 10 minutes using microphones (G.R.A.S. sound and vibrations, Vedbaek, Denmark) placed inside each cubicle and controlled by LMS (LMS CADA-X 3.5B, Data Acquisition Monitor, Troy, Mich.) software. The frequencies between 0 and 32000 Hz are recorded, saved and analysed by the same software (LMS CADA-X 3.5B, Time Data Processing Monitor and UPA (User Programming and Analysis)).

Compounds (Drugs)

All compounds (drugs) are pH-adjusted between 6.5 and 7.5 and administered at a volume of 4 ml/kg. Following compound (drug) administration, animals are returned to their original cages until time of testing.

Analysis

The recording is run through a series of statistical and Fourier analyses to filter (between 20-24 kHz) and to calculate the parameters of interest. The data are expressed as the mean±SEM. Statistical significance is assessed using T-test for comparison between naive and LPS-treated rats, and one way ANOVA followed by Dunnett's multiple comparison test (post-hoc) for drug effectiveness. A difference between groups is considered significant with a minimum p value of $\leq 0.05$. Experiments are repeated a minimum of two times.

EXAMPLES

The invention will further be described in more detail by the following Examples which describe methods whereby compounds of the present invention may be prepared, purified, analyzed and biologically tested, and which are not to be construed as limiting the invention.

Intermediate 1

N,N-Diethyl-4-formylbenzamide

To a suspension of 4-carboxybenzaldehyde (30 g, 0.2 mole) in 100 ml of toluene was added $SOCl_2$(97 ml, 1.3 moles) at 60° C. The reaction was heated until gas evolution ceased followed by evaporation to dryness with toluene (3×50 mL) This yielded a residue, which was dissolved in $CH_2Cl_2$ (200 mL). To this solution, cooled in an ice bath while stirring, was added diethylamine (50 mL). Stirring was continued for one hour and then the mixture heated at reflux for a further hour. After cooling, the mixture washed successively with $H_2O$, 2 N HCl, $H_2O$ then 2 N NaOH and finally with $H_2O$. The solution was dried over $MgSO_4$, filtered and concentrated to dryness yielding 41 g of oil. Distillation at 140-150° C./1.5 torr gave 36.9 g, 90% of INTERMEDIATE 1.

Intermediate 2 tert-Butyl 4-((3-bromophenyl){4-[(diethylamino)carbonyl]phenyl}methyl)piperazine-1-carboxylate A solution of INTERMEDIATE 1 (6.84 g, 33.3 mmol) benzotriazole (3.96 g, 33.3 mmol) and N-Boc piperidine (6.19 g, 33.3 mmol) in 200 mL of toluene was heated over night under Dean-Stark conditions. The reaction was concentrated, dissolved in 45 ml of dry THF and cooled in an ice bath. To this was cannulated 3-bromophenylzinc iodide (0.5 M in THF, 100 mL, 50 mmol) over 15 minutes. The reaction was warmed to room temperature stirred for 30 minutes then heated overnight at 50° C. The reaction mixture was quenched with $NH_4Cl$, stirred for 15 minutes then extracted 4 times with ethyl acetate. The combined organic layers were dried over $MgSO_4$, filtered and concentrated. The resulting oil was purified by flash chromatography eluting ethyl acetate/heptane 30/70 to 50/50. Yield: 5.86 g, 33% of INTERMEDIATE 2.

Intermediate 3

4-[[4-[(diethylamino)carbonyl]phenyl][3-[(methoxycarbonyl)amino]phenyl]methyl]-1-piperazinecarboxylic acid, 1,1-dimethylethyl ester To a solution of INTERMEDIATE 2 (5.39 g, 10.17 mmol) in dry dioxane, while bubbling $N_2$, was added methyl carbamate (0.99 g, 13.2 mmol), xantphos (0.47 g, 0.81 mmol), $Cs_2CO_3$ (4.63 g, 14.2 mmol) and $Pd_2(dba)_3$ (0.465 g, 0.51 mmol). The reaction was heated for 7 hrs at reflux, cooled and filtered through diatomaceous earth. The resulting oil was purified by flash chromatography 40/60 to 80/20 ethyl acetate/heptane. 3.3 g, 62% of INTERMEDIATE 3 was obtained.

Intermediate 4

[3-[[4-[(diethylamino)carbonyl]phenyl]-1-piperazinylmethyl]phenyl]-carbamic acid, methyl ester To a solution of INTERMEDIATE 3 (0.788 g, 1.5 mmol) in 15 mL of $CH_2Cl_2$ at 0° C. was added TFA (1.15 ml, 15 mmol). This was stirred until completion by HPLC. The solution was concentrated, dissolved in 20 mL of ethyl acetate and washed with 10 mL 2 N $K_2CO_3$. The organic layer was separated and the aqueous layer washed with 5×20 ml of ethyl acetate. The combined organic layers were dried over $MgSO_4$, filtered and concentrated yielding 570 mg, 89% of INTERMEDIATE 4. The INTERMEDIATE 4 was separated by chiral HPLC on Chiralpak AD 20% EtOH/80% Heptane yielding 200 mg of enantiomer INTERMEDIATE 4a and 185 mg of enantiomer INTERMEDIATE 4b.
Analytical Chiral HPLC Conditions:
Chiralpak AD 15% EtOH/85% Heptane
Flow rate 1 ml/minute
INTERMEDIATE 4a retention time 25.7 minutes
INTERMEDIATE 4b retention time 17.5 minutes Intermediate 5

4-Iodo-N,N-diethylbenzamide

To a mixture of 4-iodo-benzoyl chloride (75 g) in 500 mL $CH_2Cl_2$ was added a mixture of $Et_3N$ (50 mL) and $Et_2NH$ (100 mL) at 0° C. After the addition, the resulting reaction mixture was warmed up to room temperature in 1 hr and was then washed with saturated ammonium chloride. The organic extract was dried ($Na_2SO_4$), filtered and concentrated. Residue was recrystallized from hot hexanes to give 80 g of INTERMEDIATE 5.

Intermediate 6

4-[hydroxy(3-nitrophenyl)methyl]-N,N-diethylbenzamide

INTERMEDIATE 5, N,N-Diethyl-4-iodobenzamide (5.0 g, 16 mmol), was dissolved in THF (150 mL) and cooled to −78° C. under nitrogen atmosphere. n-BuLi (15 mL, 1.07 M solution in hexane, 16 mmol) was added dropwise during 10 min at −65 to −78° C. The solution was then cannulated into 3-nitrobenzaldehyde (2.4 g, 16 mmol) in toluene/THF (approx. 1:1, 100 mL) at −78° C. $NH_4Cl$ (aq.) was added after 30 min. After concentration in vacuo, extraction with EtOAc/water, drying ($MgSO_4$) and evaporation of the organic phase, the residue was purified by chromatography on silica (0-75% EtOAc/heptane) to give INTERMEDIATE 6 (2.6 g, 50%). $^1$H NMR ($CDCl_3$) δ 1.0-1.3 (m, 6H), 3.2, 3.5 (2 m, 4H), 5.90 (s, 1H), 7.30-7.40 (m, 4H), 7.50 (m, 1H), 7.70 (d, J=8 Hz, 1H), 8.12 (m, 1H), 8.28 (m, 1H).

Intermediate 7

Racemic N,N-diethyl-4-[(3-nitrophenyl)(1-piperazinyl)methyl]benzamide

To a solution of INTERMEDIATE 6 (10.01 g, 30.5 mmol) in dichloromethane (200 mL) was added thionyl bromide (2.58 mL, 33.6 mmol). After one hour at room temperature the reaction washed with saturated aqueous sodium bicarbonate (100 mL) and the organic layer was separated. The aqueous layer was washed with dichloromethane (3×100 mL) and the combined organic extracts were dried ($Na_2SO_4$), filtered and concentrated.
The resulting product in the organic extracts was dissolved in acetonitrile (350 mL) and piperazine (10.5 g, 122 mmol) was added. After heating the reaction for one hour at 65° C. the reaction washed with saturated ammonium chloride/ethyl acetate and the organic layer was separated. The aqueous layer was extracted with ethyl acetate (3×100 mL) and the combined organic extracts were dried ($Na_2SO_4$), filtered and concentrated to give racemic INTERMEDIATE 7.

Intermediate 8

(−)-N,N-diethyl-4-[(3-nitrophenyl)(1-piperazinyl)methyl]benzamide

Racemic INTERMEDIATE 7 is resolved to give enantiomerically pure INTERMEDIATE 8 as follows:

INTERMEDIATE 7 was dissolved in ethanol (150 mL) and di-p-toluoyl-D-tartaric acid (11.79 g, 1 equivalent) was added. The product precipitated out over a 12 hour period. The solid was collected by filtration and was redissolved in refluxing ethanol until all of the solid dissolved (approximately 1200 mL ethanol). Upon cooling the solid was collected by filtration and the recrystallation repeated a second time. The solid was collected by filtration and was treated with aqueous sodium hydroxide (2M) and was extracted with ethyl acetate. The organic extract was then dried ($Na_2SO_4$), filtered and concentrated to give 1.986 g of enantiomerically pure INTERMEDIATE 8. $^1$H NMR ($CDCl_3$) δ 1.11 (br s, 3H), 1.25 (br s, 3H), 2.37 (br s, 4H), 2.91 (t, J=5 Hz, 4H), 3.23 (br s, 2H), 3.52 (br s, 2H), 4.38 (s, 1H), 7.31-7.33 (m, 2H), 7.41-7.43 (m, 2H), 7.47 (t, J=8 Hz, 1H), 7.75-7.79 (m, 1H), 8.06-8.09 (m, 1H), 8.30-8.32 (m, 1H).

Chiral purity was determined by HPLC using the following conditions:
Chiralpack AD column (Daicel Chemical Industries)
Flow rate 1 ml/minute
Run time 30 minutes at 25° C.
Isocratic 15% ethanol 85% hexanes
Retention time of molecule=20 minutes
INTERMEDIATE 9 may be obtained by the above procedure but using di-p-toluoyl-L-tartaric acid in place of di-p-toluoyl-D-tartaric acid.

Intermediate 10

N,N-diethyl-4-[(3-nitrophenyl)[4-(phenylmethyl)-1-piperazinyl]methyl]-benzamide

To a solution of INTERMEDIATE 8 (1.407 g, 3.55 mmol) in 1,2-dichloroethane (30 mL) was added benzaldehyde (0.58 mL, 5.71 mmol) and sodium triacetoxyborohydride (1.21 g, 5.71 mmol). After 20 hours at room temperature the reaction was quenched with aqueous sodium bicarbonate and the organic layer was separated. The aqueous layer was extracted with dichloromethane (3×50 mL) and the combined organic extracts were dried ($Na_2SO_4$), filtered and concentrated. The residue was purified by flash chromatography, eluting 5% methanol in dichloromethane to give INTERMEDIATE 10 as a colourless foam (1.576 g, 91% yield).

Intermediate 11

4-[(3-aminophenyl)[4-(phenylmethyl)-1-piperazinyl]methyl]-N,N-diethyl-benzamide

To a solution of INTERMEDIATE 10 (1.576 g, 3.24 mmol) in a mixture of ethanol, tetrahydrofuran, water and aqueous saturated ammonium chloride (4:2:1:1 ratio v/v) (30 mL) was added granules of iron (1.80 g, 32.4 mmol). After 4 hours at reflux (90° C.) the reaction was cooled to room temperature, filtered through celite and concentrated. To the residue was added aqueous sodium bicarbonate and dichloromethane. The organic layer was separated and the aqueous layer was extracted with dichloromethane (3×50 mL) and the combined organic extracts were dried ($Na_2SO_4$), filtered and concentrated. The product was purified on silica gel eluting with 1% to 5% methanol in dichloromethane to afford INTERMEDIATE 11 (1.310 g, 88% yield).
Chiral HPLC conditions:
Chiralpack AD column (Daicel Chemical Industries)
Flow rate: 1 ml/minute
Run time 30 minutes at 25° C.
Isocratic 30% isopropanol/70% hexane
Retention time of molecule=18.7 minutes

Intermediate 14

4-{(S)-(3-aminophenyl) [4-(pyridin-3-ylmethyl)piperazin-1-yl]methyl}-N,N-diethylbenzamide To a solution of INTERMEDIATE 9 (452 mg) in 1,2-dichloroethane (10 ml) was added 3-pyridine carboxaldehyde (215 µL; 2 eq) and sodium triacetoxyborohydride (483 mg; 2 eq). The reaction was stirred at room temperature under nitrogen for 18 hours and concentrated. Saturated sodium bicarbonate was added and the aqueous solution was extracted with three portions of dichloromethane and the combined organics were dried over anhydrous sodium sulfate, filtered and concentrated to yield INTERMEDIATE 12. The crude INTERMEDIATE 12 was dissolved in a mixture of ethanol, tetrahydrofuran, water and saturated ammonium chloride (4 ml; ratios 4:2:1:1 v/v). Iron nanoparticules (3 tips of spatula) were added and the solution was heated at 150° C. for 10 minutes in the microwave. The resulting mixture was cooled, filtered through celite and concentrated. The residue was purified by flash chromatography on silica gel, eluting with a gradient from 1% to 10% MeOH in dichloromethane to give INTERMEDIATE 14 (312 mg, 60% yield) as a colourless solid.

Intermediate 15

4-{(S)-(3-aminophenyl) [4-(1,3-thiazol-2-ylmethyl)piperazin-1-yl]methyl}-N,N-diethylbenzamide To a solution of INTERMEDIATE 9 (479 mg) in 1,2-dichloroethane (13 ml) was added 2-thiazole carboxaldehyde (212 µL; 2 eq) and sodium triacetoxyborohydride (510 mg; 2 eq). The reaction was stirred at room temperature under nitrogen for 18 hours. Saturated sodium bicarbonate was added and the aqueous solution was extracted with three portions of dichloromethane and the combined organics were dried over anhydrous sodium sulfate, filtered and concentrated to give INTERMEDIATE 13. The crude INTERMEDIATE 13 was dissolved in a mixture of ethanol, tetrahydrofuran, water and saturated ammonium chloride (4 ml; ratios 4:2:1:1 v/v). Iron nanoparticules (3 tips of spatula) were added and the solution was heated at 150° C. for 10 minutes in the microwave. The resulting mixture was cooled, filtered through celite and concentrated. The residue was purified by reverse phase chromatography, eluting 10% to 45% acetonitrile in water containing 0.1% trifluoroacetic acid. The product was obtained as the trifluoroacetic acid salt and was lyophilized to give INTERMEDIATE 15 (372 mg, 39% yield) as a colourless solid.

Intermediate 16a or 16b tert-Butyl 4-((3-aminophenyl){4-[(diethylamino) carbonyl]phenyl}methyl)piperazine-1-carboxylate To a solution of INTERMEDIATE 8 or 9 (300 mg) in dioxane (40 ml) was added di-tert-butyl dicarbonate (247 mg; 1.5 eq). Sodium carbonate (119 mg; 1.5 eq) was dissolved in water (15 ml) and then added in the dioxane solution. After 12 hours the solution was concentrated and saturated sodium bicarbonate was then added. The aqueous solution was extracted with three portions of dichloromethane and the combined organics were dried over anhydrous sodium sulfate, filtered and concentrated to afford a white foam. Without further purification, the foam was then dissolved in a mixture of ethanol, tetrahydrofuran, water and saturated ammonium chloride (15 ml; ratios 4:2:1:1 v/v). Iron granules (422 mg; 10 eq) were added and the solution was heated at 90° C. for 1.5 hour. The resulting mixture was cooled, filtered through celite and concentrated. Saturated sodium bicarbonate was added and the aqueous solution was extracted with three portions of dichloromethane and the combined organics were dried over anhydrous sodium sulfate, filtered and concentrated to afford a white foam INTERMEDIATE 16a or 16b, respectively. The product can be use without any further purification. (92-99% yield). $^1$H NMR (400 MHz, CDCl$_3$) 1.06-1.16 (m, 3H), 1.17-1.26 (m, 3H), 1.44 (s, 9H), 2.28-2.39 (m, 4H), 3.20-3.31 (br s, 2H), 3.37-3.44 (br s, 2H), 3.48-3.58 (br s, 2H), 3.60-3.70 (br s, 2H), 4.12 (s, 1H), 6.51-6.55 (m, 1H), 6.72 (t, J=2.13 Hz, 1H), 6.79 (d, J=8.17 Hz, 1H), 7.06 (t, J=7.46 Hz, 1H), 7.29 (d, J=7.82 Hz, 2H), 7.43 (d, J=7.82 Hz, 2H).

Compound 1

R-Methyl 3-[(4-[(diethylamino)carbonyl]phenyl)(4-benzyl-piperazin-1-yl)methyl]phenylcarbamate

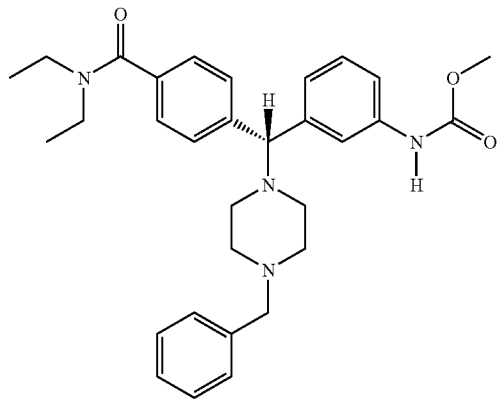

To a solution of INTERMEDIATE 4a (200 mg, 0.47 mmol) dissolved in 5 ml dichloroethane was added benzaldehyde (95.5 µL, 0.94 mmol) and NaBH(OAc)$_3$ (200 mg, 0.94 mmol). The reaction was stirred at room temperature overnight. Then 5 ml of a saturated solution of NaHCO$_3$ was added and the aqueous layer extracted 4 times with CH$_2$Cl$_2$. The combined organic layers were dried over MgSO$_4$, filtered and concentrated. Purification by reverse phase chromatography yielded 188 mg of COMPOUND 1 under the conditions: LUNA C-18, gradient 10-50% B in 25 min, flow: 40 mL/min, 20° C., A: 0.1% TFA in H$_2$O, B: 0.1% TFA in CH$_3$CN. $^1$H NMR (400 MHz, CD$_3$OD): δ 1.08 (m, 3H), 1.21 (m, 3H), 2.31 (m, 2H), 3.04 (m, 2H), 3.24 (m, 4H), 3.39 (m, 2H), 3.51 (m, 2H), 3.72 (s, 3H), 4.34 (s, 2H), 4.43 (s, 1H), 7.09 (m, 1H), 7.20 (m, 2H), 7.32 (d, J=8.2 Hz, 2 H), 7.48 (s, 5H), 7.55 (d, J=8.2 Hz, 2 H), 7.70 (s, 1H). Anal. calcd for C$_{31}$H$_{38}$N$_4$O$_3$×2.10 C$_2$HF$_3$O$_2$×0.3H$_2$O: C, 55.66; H, 5.40; N, 7.38. Found: C, 55.70; H, 5.24; N, 7.41. M.S (calcd): 515.30 (MH+), M.S (found): 515.55 (MH+). HPLC: k': 2.95; Purity: >99% (215 nm), >99% (254 nm), >99% (280 nm). Conditions: Zorbax C-18, gradient 30-80% B in 25 min, flow: 1 mL/min, 25° C., A: 0.1% TFA in H$_2$O, B: 0.1% TFA in CH$_3$CN; Chiral Purity: >90% (215 nm), >94% (254 nm), >94% (280 nm), Rt: 8.7 mins; Conditions: Chiralpak AD 30% IPA/70% hexane. Rotation: $[\alpha]^{17}_D$=−14.5° (c=0.74, EtOH).

Compound 1

R-[3-[[4-[(diethylamino)carbonyl]phenyl][4-(phenylmethyl)-1-piperazinyl]methyl]phenyl]-carbamic acid methyl ester (via another synthetic route)

Methyl chloroformate (0.008 mL, 0.11 mmol) and zinc dust (8 mg, 0.11 mmol) were stirred together in 1 mL of dry toluene at room temperature under nitrogen for 10 minutes. A 1 mL toluene solution of INTERMEDIATE 10 (50 mg, 0.110 mmol) was then added dropwise and the reaction mixture was stirred at room temperature overnight. The solution was then diluted with dichloromethane and filtered. The organic phase washed with saturated NaHCO$_3$ solution, brine and dried over anhydrous Na$_2$SO$_4$. The product was purified by silica gel flash chromatography eluting 50% hexanes in acetone to afford COMPOUND 1 (28 mg, 50% yield). $^1$H NMR (400 MHz, CD$_3$OD): δ 1.08 (m, 3H), 1.21 (m, 3H), 2.31 (m, 2H), 3.04 (m, 2H), 3.24 (m, 4H), 3.39 (m, 2H), 3.51 (m, 2H), 3.72 (s, 3H), 4.34 (s, 2H), 4.43 (s, 1H), 7.09 (m, 1H), 7.20 (m, 2H), 7.32 (d, J=8.2 Hz, 2 H), 7.48 (s, 5H), 7.55 (d, J=8.2 Hz, 2 H), 7.70 (s, 1H). Anal. calcd for C$_{31}$H$_{38}$N$_4$O$_3$×2.10 C$_2$HF$_3$O$_2$× 0.3H$_2$O: C, 55.66; H, 5.40; N, 7.38. Found: C, 55.70; H, 5.24; N, 7.41. M.S (calcd): 515.30 (MH+), M.S (found): 515.55 (MH+). HPLC: k': 2.95; Purity: >99% (215 nm), >99% (254 nm), >99% (280 nm). Conditions: Zorbax C-18, gradient 30-80% B in 25 min, flow: 1 mL/min, 25° C., A: 0.1% TFA in H$_2$O, B: 0.1% TFA in CH$_3$CN; Chiral Purity: >90% (215 nm)>94% (254 nm)>94% (280 nm), Retention time: 8.7 mins; Conditions: Chiralpak AD 30% IPA/70% hexane. Rotation: $[α]^{17}_D$=−14.5° (c=0.74, EtOH).

Compound 2

S-Methyl 3-[(4-[(diethylamino)carbonyl]phenyl)(4-benzyl-piperazin-1-yl)methyl]phenylcarbamate

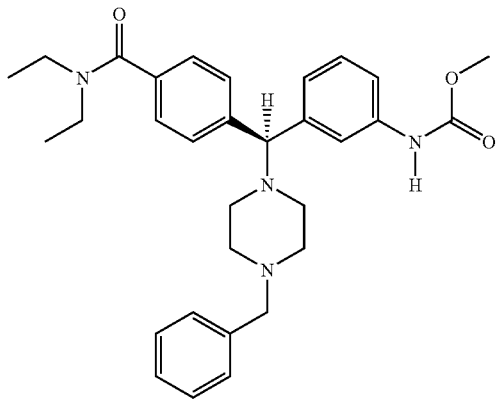

Using the same method as for COMPOUND 1 and using INTERMEDIATE 4b (185 mg, 0.43 mmol) and benzaldehyde (100 □L, 0.87 mmol) afforded 178 mg of COMPOUND 2. $^1$H NMR (400 MHz, CD$_3$OD): δ 1.09 (m, 3H), 1.22 (m, 3H), 2.31 (m, 2H), 3.04 (m, 2H), 3.24 (m, 4H), 3.40 (m, 2H), 3.51 (m, 2H), 3.72 (s, 3H), 4.34 (s, 2H), 4.43 (s, 1H), 7.09 (m, 1H), 7.19 (m, 2H), 7.32 (d, J=8.2 Hz, 2 H), 7.48 (s, 5H), 7.55 (d, J=8.2 Hz, 2 H), 7.71 (s, 1H). Anal. calcd for C$_{31}$H$_{38}$N$_4$O$_3$× 1.60 C$_2$HF$_3$O$_2$×0.6H$_2$O: C, 58.47; H, 5.77 N, 7.98. Found: C, 58.50; H, 5.70; N, 8.06. M.S (calcd): 515.30 (MH+), M.S (found): 515.57 (MH+). HPLC: k': 3.00; Purity: >99% (215 nm), >99% (254 nm), >99% (280 nm). HPLC Conditions: Zorbax C-18, gradient 30-80% B in 25 min, flow: 1 mL/min, 25° C., A: 0.1% TFA in H$_2$O, B: 0.1% TFA in CH$_3$CN; Chiral Purity: >99% (215 nm)>99% (254 nm)>99% (280 nm), Rt: 11.2 min; Chiral HPLC Conditions: Chiralpak AD, 30% IPA/70% hexane. Rotation: $[α]^{17}_D$=+17.1° (c=0.77, EtOH).

Compound 3

S-Methyl 3-{{4-[(diethylamino)carbonyl]phenyl}[4-(thien-2-ylmethyl)piperazin-1-yl] methyl}phenylcarbamate

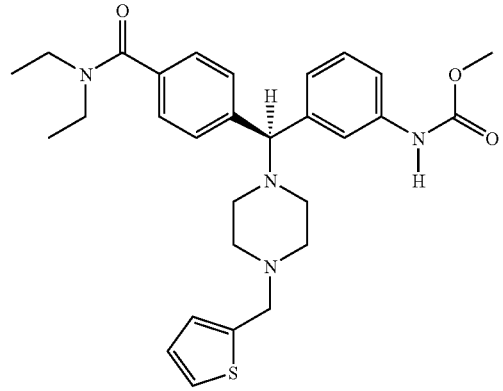

Using the same method as for COMPOUND 1 and using INTERMEDIATE 4b (200 mg, 0.47 mmol) and 2-thiophenecarboxaldehyde (66 □L, 0.70 mmol) afforded 213 mg of COMPOUND 3. $^1$H NMR (400 MHz, CD$_3$OD): δ 1.08 (m, 3H), 1.21 (m, 3H), 2.35 (br s, 2H), 3.04 (br s, 2H), 3.32 (m, 6H), 3.51 (m, 2H), 3.72 (s, 3H), 4.44 (s, 1H), 4.58 (s, 2H), 7.09 (m, 1H), 7.13 (dd, J=3.7, J=5.1 Hz, 3H), 7.21 (m, 2 H), 7.32 (m, 3 H), 7.55 (d, J=8.2 Hz, 2 H), 7.62 (m, 1 H), 7.69 (br s, 1H). Anal. calcd for C$_{29}$H$_{36}$N$_4$O$_3$S×1.40 C$_2$HF$_3$O$_2$×0.9H$_2$O: C, 54.84; H, 5.67; N, 8.04. Found: C, 54.76; H, 5.65; N, 8.09. M.S (calcd): 521.26 (MH$^+$), M.S (found): 521.26 (MH$^+$). HPLC: k': 6.51; Purity: >99% (215 nm), >99% (254 nm), >99% (280 nm). HPLC Conditions: Zorbax C-18, gradient 30-80% B in 25 min, flow: 1 mL/min, 25° C., A: 0.1% TFA in H$_2$O, B: 0.1% TFA in CH$_3$CN; Chiral Purity: >97% (215 nm)>96% (254 nm)>96% (280 nm), Rt: 22.2 min; Chiral HPLC Conditions: Chiralpak AD, 30% IPA/70% hexane. Rotation: $[α]^{17}_D$=+11.3° (c=1.14, MeOH).

Compound 4

R-Methyl 3-{{4-[(diethylamino)carbonyl]phenyl}[4-(thien-2-ylmethyl)piperazin-1-yl] methyl}phenylcarbamate

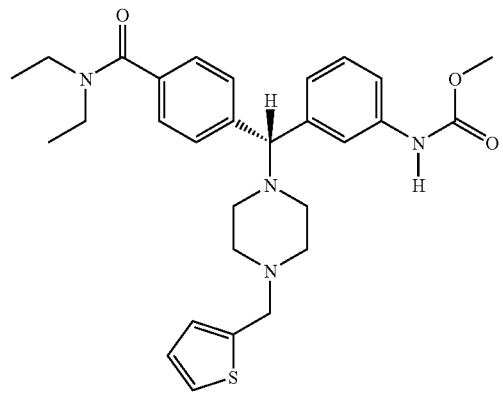

Using the same method as for COMPOUND 1 and using INTERMEDIATE 4a (200 mg, 0.47 mmol) and 2-thiophenecarboxaldehyde (66 □L, 0.70 mmol) afforded 197 mg of COMPOUND 4. $^1$H NMR (400 MHz, CD$_3$OD): δ 1.08 (m, 3H), 1.21 (m, 3H), 2.35 (br s, 2H), 3.02 (br s, 2H), 3.32 (m, 6H), 3.51 (m, 2H), 3.72 (s, 3H), 4.44 (s, 1H), 4.58 (s, 2H), 7.09 (m, 1H), 7.13 (m, 1H), 7.21 (m, 2H), 7.32 (m, 3H), 7.55 (d, J=8.0 Hz, 2H), 7.62 (d, J=5.1 Hz, 2H), 7.69 (s, 1H). Anal. calcd for C$_{29}$H$_{36}$N$_4$O$_3$S×1.5 C$_2$HF$_3$O$_2$×0.9H$_2$O: C, 55.13; H, 5.51; N, 8.04. Found: C, 55.14; H, 5.55; N, 8.11. M.S (calcd):

521.26 (MH+), M.S. (found): 521.23 (MH+). HPLC: k': 6.59; Purity: >99% (215 nm), >99% (254 nm), >99% (280 nm). HPLC Conditions: Zorbax C-18, gradient 20-50% B in 25 min, flow: 1 mL/min, 25° C., A: 0.1% TFA in H₂O, B: 0.1% TFA in CH₃CN; Chiral Purity: >99% (215 nm)>99% (254 nm)>99% (280 nm), Retention time: 11.8 min; Chiral HPLC Conditions: Chiralpak AD, 30% IPA/70% hexane. Rotation: $[\alpha]^{17}_D$=−12.8° (c=0.96, MeOH).

Compound 5

S-Methyl 3-{{4-[(diethylamino)carbonyl]phenyl}[4-(thien-3-ylmethyl)piperazin-1-yl]methyl}phenylcarbamate

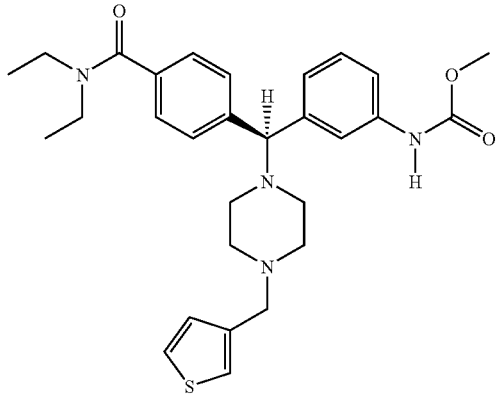

Using the same method as for COMPOUND 1 and using INTERMEDIATE 4b (200 mg, 0.47 mmol) and 3-thiophenecarboxaldehyde (66 μL, 0.70 mmol) afforded 205 mg of COMPOUND 5. ¹H NMR (400 MHz, CD₃OD): δ 1.08 (m, 3H), 1.21 (m, 3H), 2.36 (m, 2H), 2.99 (m, 2H), 3.28 (m, 6H), 3.51 (m, 2H), 3.72 (s, 3H), 4.36 (s, 2H), 4.42 (s, 1H), 7.09 (m, 1H), 7.21 (m, 3H), 7.32 (d, J=8.0 Hz, 2 H), 7.55 (m, 3H), 7.67 (m, 2H). Anal. calcd for C₂₉H₃₆N₄O₃S×1.7 C₂HF₃O₂×0.3H₂O: C, 54.05; H, 5.36; N, 7.78. Found: C, 54.08; H, 5.36; N, 7.70. M.S. (calcd): 521.26 (MHV), M.S. (found): 521.26 (MH+). HPLC: k': 6.68; Purity: >99% (215 nm), >99% (254 nm), >99% (280 nm). HPLC Conditions: Zorbax C-18, gradient 20-50% B in 25 min, flow: 1 mL/min, 25° C., A: 0.1% TFA in H₂O, B: 0.1% TFA in CH₃CN; Chiral Purity: >99% (215 nm), >99% (254 nm), >99% (280 nm), Retention time: 13.3 min; Chiral HPLC Conditions: Chiralpak AD, 30% IPA/70% hexane. Rotation: $[\alpha]^{17}_D$=+11.3° (c=1.15, MeOH).

Compound 6

R-Methyl 3-{{4-[(diethylamino)carbonyl]phenyl}[4-(thien-3-ylmethyl)piperazin-1-yl]methyl}phenylcarbamate

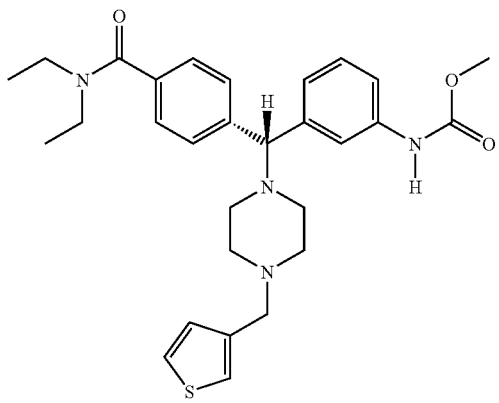

Using the same method as for COMPOUND 1 and using INTERMEDIATE 4a (200 mg, 0.47 mmol) and 3-thiophenecarboxaldehyde (66 μL, 0.70 mmol) afforded 199 mg of COMPOUND 6. ¹H NMR (400 MHz, CD₃OD): δ 1.08 (m, 3H), 1.21 (m, 3H), 2.31 (br s, 2H), 3.04 (br s, 2H), 3.24 (m, 4H), 3.37 (m, 2H), 3.51 (m, 2H), 3.72 (s, 3H), 4.37 (s, 2H), 4.43 (s, 1H), 7.09 (m, 1H), 7.21 (m, 3H), 7.32 (d, J=8.2 Hz, 2H), 7.55 (m, 3 H), 7.68 (m, 2H). Anal. calcd for C₂₉H₃₆N₄O₃S×1.4 C₂HF₃O₂×1.0H₂O: C, 54.69; H, 5.69; N, 8.02. Found: C, 54.74; H, 5.63; N, 8.16. M.S. (calcd): 521.26 (MH+), M.S. (found): 521.25 (MH+). HPLC: k': 6.67; Purity: >99% (215 nm), >99% (254 nm), >99% (280 nm). HPLC Conditions: Zorbax C-18, gradient 20-50% B in 25 min, flow: 1 mL/min, 25° C., A: 0.1% TFA in H₂O, B: 0.1% TFA in CH₃CN; Chiral Purity: >99% (215 nm)>99% (254 nm)>99% (280 nm), Retention time: 9.0 min; Chiral HPLC Conditions: Chiralpak AD, 30% IPA/70% hexane. Rotation: $[\alpha]^{17}_D$=−12.9° (c=1.13, MeOH).

Compound 7

S-Methyl 3-{{4-[(diethylamino)carbonyl]phenyl}[4-(2-furylmethyl)piperazin-1-yl]methyl}phenylcarbamate

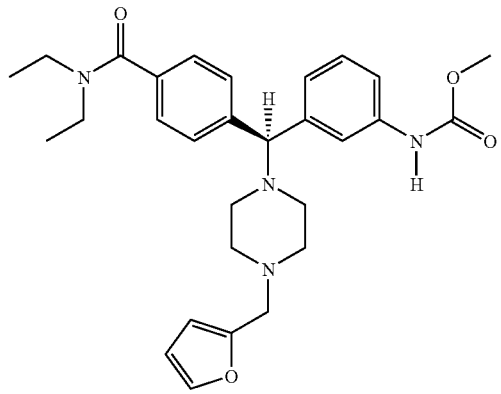

Using the same method as for COMPOUND 1 and using INTERMEDIATE 4b (200 mg, 0.47 mmol) and 2-furaldehyde (58 μL, 0.70 mmol) afforded 172 mg of COMPOUND 7. ¹H NMR (400 MHz, CD₃OD): δ 1.08 (m, 3H), 1.22 (m, 3H), 2.36 (br s, 2H), 3.02 (br s, 2H), 3.31 (m, 6H), 3.51 (m, 2H), 3.72 (s, 3H), 4.42 (s, 2H), 4.44 (s, 1H), 6.52 (dd, J=1.9, 3.1 Hz, 1H), 6.71 (d, J=3.3 Hz, 1H), 7.09 (m, 1H), 7.20 (m, 2H), 7.32 (d, J=8.4 Hz, 2H), 7.55 (d, J=8.2 Hz, 2H), 7.66 (m, 1H), 7.69 (s, 1H).

Anal. calcd for C₂₉H₃₆N₄O₄×1.5 C₂HF₃O₂×0.6H₂O: C, 55.99; H, 5.68; N, 8.16.

Found: C, 56.02; H, 5.74; N, 8.22. M.S. (calcd): 505.28 (MH+), M.S. (found): 505.26 (MH+). HPLC: k': 5.92; Purity: >99% (215 nm), >99% (254 nm), >99% (280 nm). HPLC Conditions: Zorbax C-18, gradient 20-50% B in 25 min, flow: 1 mL/min, 25° C., A: 0.1% TFA in H₂O, B: 0.1% TFA in CH₃CN; Chiral Purity: >95% (215 nm), >95% (254 nm), >96% (280 nm), Rt: 8.3 min; Chiral HPLC Conditions: Chiralpak AD, 30% IPA/70% hexane. Rotation: $[\alpha]^{17}_D$=+14.4° (c=1.06, MeOH).

Compound 8

R-Methyl 3-{{4-[(diethylamino)carbonyl]phenyl}[4-(2-furylmethyl)piperazin-1-yl]methyl}phenylcarbamate

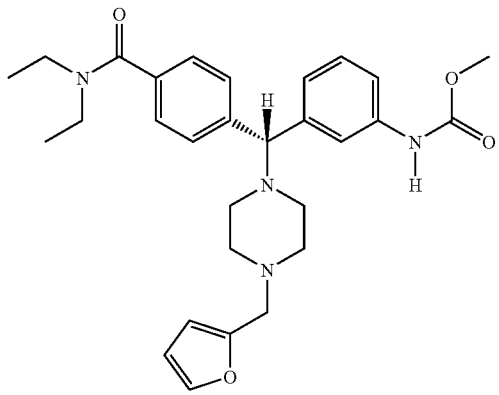

Using the same method as for COMPOUND 1 and using INTERMEDIATE 4a (200 mg, 0.47 mmol) and 2-furaldehyde (58 □L, 0.70 mmol) afforded 50 mg of COMPOUND 8. $^1$H NMR (400 MHz, CD$_3$OD): δ 1.09 (m, 3H), 1.22 (m, 3H), 2.32 (br s, 2H), 3.06 (br s, 2H), 3.24 (m, 4H), 3.40 (m, 2H), 3.51 (m, 2H), 3.72 (s, 3H), 4.42 (s, 2H), 4.44 (s, 1H), 6.53 (dd, J=1.8, 3.1 Hz, 1H), 6.71 (d, J=3.3 Hz, 1H), 7.09 (m, 1H), 7.20 (m, 2H), 7.32 (d, J=8.2 Hz, 2H), 7.55 (d, J=8.2 Hz, 2H), 7.67 (m, 1H), 7.70 (s, 1H). Anal. calcd for C$_{29}$H$_{36}$N$_4$O$_4$×1.6 C$_2$HF$_3$O$_2$×0.3H$_2$O: C, 55.85; H, 5.56; N, 8.09. Found: C, 55.76; H, 5.50; N, 8.25. M.S. (calcd): 505.28 (MH$^+$), M.S. (found): 505.27 (MH$^+$). HPLC: k': 6.00; Purity: >99% (215 nm), >99% (254 nm), >99% (280 nm). HPLC Conditions: Zorbax C-18, gradient 20-50% B in 25 min, flow: 1 mL/min, 25° C., A: 0.1% TFA in H$_2$O, B: 0.1% TFA in CH$_3$CN; Chiral Purity: >99% (215 nm), >99% (254 nm), >99% (280 nm), Retention time: 7.2 min; Chiral HPLC Conditions: Chiralpak AD, 30% IPA/70% hexane. Rotation: [α]$^{17}_D$=−13.8° (c=0.97, MeOH).

Compound 9

S-Methyl 3-{{4-[(diethylamino)carbonyl]phenyl}[4-(3-furylmethyl)piperazin-1-yl]methyl}phenylcarbamate

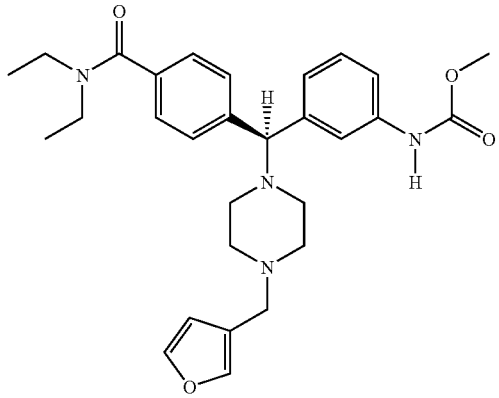

Using the same method as for COMPOUND 1 and using INTERMEDIATE 4b (200 mg, 0.47 mmol) and 3-furaldehyde (58 □L, 0.70 mmol) afforded 167 mg of COMPOUND 9. $^1$H NMR (400 MHz, CD$_3$OD): δ 1.09 (m, 3H), 1.22 (m, 3H), 2.32 (br s, 2H), 3.06 (br s, 2H), 3.24 (m, 4H), 3.40 (m, 2H), 3.51 (m, 2H), 3.72 (s, 3H), 4.42 (s, 2H), 4.44 (s, 1H), 6.53 (dd, J=1.8, 3.1 Hz, 1H), 6.71 (d, J=3.3 Hz, 1H), 7.09 (m, 1H), 7.20 (m, 2H), 7.32 (d, J=8.2 Hz, 2H), 7.55 (d, J=8.2 Hz, 2H), 7.67 (m, 1H), 7.70 (s, 1H). Anal. calcd for C$_{29}$H$_{36}$N$_4$O$_4$×2.0 C$_2$HF$_3$O$_2$×0.5H$_2$O: C, 53.44; H, 5.30; N, 7.55. Found: C, 53.42; H, 5.28; N, 7.68. M.S. (calcd): 505.28 (MH$^+$), M.S. (found): 505.27 (MH$^+$). HPLC: k': 5.99; Purity: >99% (215 nm), >99% (254 nm), >99% (280 nm). HPLC Conditions: Zorbax C-18, gradient 20-50% B in 25 min, flow: 1 mL/min, 25° C., A: 0.1% TFA in H$_2$O, B: 0.1% TFA in CH$_3$CN; Chiral Purity: >97% (215 nm)>97% (254 nm)>97% (280 nm), Rt: 13.8 min; Chiral HPLC Conditions: Chiralpak AD, 30% IPA/70% hexane. Rotation: [α]$^{17}_D$=+13.9° (c=0.94, MeOH).

Compound 10

R-Methyl 3-{{4-[(diethylamino)carbonyl]phenyl}[4-(3-furylmethyl)piperazin-1-yl]methyl}phenylcarbamate

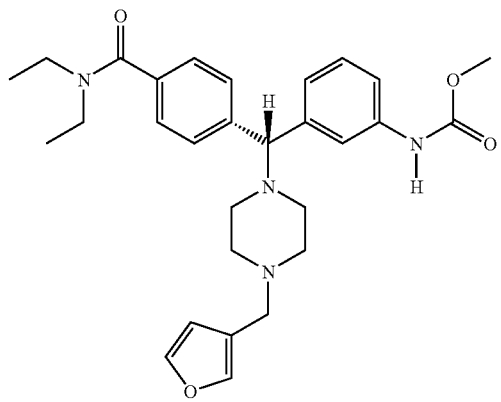

Using the same method as for COMPOUND 1 and using INTERMEDIATE 4a (200 mg, 0.47 mmol) and 3-furaldehyde (58 μL, 0.70 mmol) afforded 119 mg of COMPOUND 10. $^1$H NMR (400 MHz, CD$_3$OD): δ 1.09 (m, 3H), 1.22 (m, 3H), 2.32 (br s, 2H), 3.05 (br s, 2H), 3.21 (m, 4H), 3.47 (m, 4H), 3.72 (s, 3H), 4.24 (s, 2H), 4.43 (s, 1H), 6.58 (m, 1 H), 7.09 (m, 1H), 7.20 (m, 2H), 7.32 (d, J=8.2 Hz, 2 H), 7.55 (d, J=8.2 Hz, 2 H), 7.63 (m, 1H), 7.70 (s, 1H), 7.76 (s, 1H). Anal. Calcd for C$_{29}$H$_{36}$N$_4$O$_4$×1.5 C$_2$HF$_3$O$_2$×0.2H$_2$O: C, 56.58; H, 5.62; N, 8.25. Found: C, 56.50; H, 5.56; N, 8.31. M.S. (calcd): 505.28 (MH$^+$), M.S. (found): 505.27 (MH$^+$). HPLC: k': 6.02; Purity: >99% (215 nm), >99% (254 nm), >99% (280 nm). HPLC Conditions: Zorbax C-18, gradient 20-50% B in 25 min, flow: 1 mL/min, 25° C., A: 0.1% TFA in H$_2$O, B: 0.1% TFA in CH$_3$CN; Chiral Purity: >99% (215 nm), >99% (254 nm), >99% (280 nm), Retention time: 8.7 min; Chiral HPLC Conditions: Chiralpak AD, 30% IPA/70% hexane. Rotation: [α]$^{17}_D$=−14.9° (c=1.10, MeOH).

Compound 11

R-Methyl 3-{{4-[(diethylamino)carbonyl]phenyl}[4-(1H-imidazol-2-ylmethyl)piperazin-1-yl]methyl}phenylcarbamate

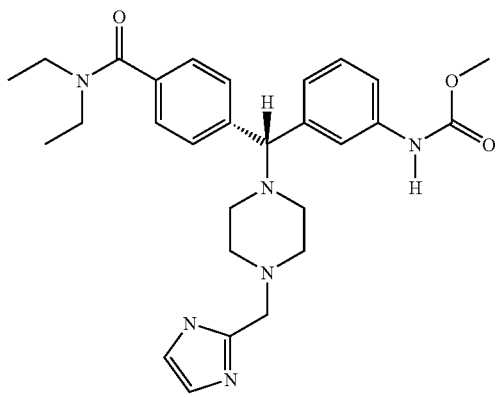

Using the same method as for COMPOUND 1 and using INTERMEDIATE 4a (200 mg, 0.47 mmol) and 2-imidazole-carboxaldehyde (68 mg, 0.70 mmol) afforded 141 mg of COMPOUND 11. $^1$H NMR (400 MHz, CD$_3$OD): δ 1.09 (m, 3H), 1.23 (m, 3H), 2.82 (br s, 4H), 3.02 (br s, 4H), 3.24 (m, 2H), 3.52 (m, 2H), 3.73 (s, 3H), 3.98 (s, 2H), 5.03 (s, 1H), 7.27 (m, 3H), 7.42 (d, J=8.0 Hz, 2 H), 7.49 (m, 2H), 7.67 (d, J=8.0 Hz, 2 H), 7.84 (s, 1H). Anal. calcd for C$_{28}$H$_{36}$N$_6$O$_3$×2.1 C$_2$HF$_3$O$_2$×1.5H$_2$O: C, 50.16; H, 5.37; N, 10.90. Found: C, 50.06; H, 5.27; N, 11.02. M.S. (calcd): 505.29 (MH$^+$), M.S. (found): 505.28 (MH$^+$). HPLC: k': 2.55; Purity: >98% (215 nm), >97% (254 nm), >97% (280 nm). HPLC Conditions: Zorbax C-18, gradient 20-50% B in 25 min, flow: 1 mL/min, 25° C., A: 0.1% TFA in H$_2$O, B: 0.1% TFA in CH$_3$CN; Chiral Purity: >99% (215 nm), >99% (254 nm), >99% (280 nm), Retention time: 12.5 min; Chiral HPLC Conditions: Chiralpak AD, 30% IPA/70% hexane. Rotation: $[α]^{16}_D$=−3.33° (c=1.08, MeOH).

Compound 12

S-Methyl3-{{4-[(diethylamino)carbonyl]phenyl}[4-(pyridin-2-ylmethyl)piperazin-1-yl]methyl}phenylcarbamate

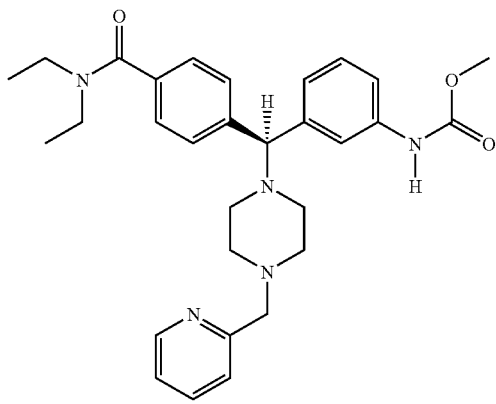

Using the same method as for COMPOUND 1 and using INTERMEDIATE 4b (200 mg, 0.47 mmol) and 2-pyridine carboxaldehyde (76 mg, 0.70 mmol) afforded 213 mg of COMPOUND 12. $^1$H NMR (400 MHz, CD$_3$OD): δ 1.08 (m, 3H), 1.22 (m, 3H), 2.74 (br s, 4H), 3.24 (m, 2H), 3.41 (m, 4H), 3.51 (m, 2H), 3.72 (s, 3H), 4.48 (s, 2H), 4.48 (s, 1H), 7.11 (m, 1H), 7.21 (m, 2H), 7.33 (d, J=7.7 Hz, 2 H), 7.43 (m, 1H), 7.48 (m, 1H), 7.57 (d, J=7.7 Hz, 2 H), 7.73 (s, 1H), 7.89 (s, 1H), 8.66 (m, 1H). Anal. calcd for C$_{30}$H$_{37}$N$_5$O$_3$ 1.5 C$_2$HF$_3$O$_2$× 1.2H$_2$O: C, 55.96; H, 5.82; N, 10.01. Found: C, 55.93; H, 5.73; N, 10.01. M.S. (calcd): 516.30 (MH$^+$), M.S. (found): 516.29 (MH$^+$). HPLC: k': 0.88; Purity: >99% (215 nm), >99% (254 nm), >99% (280 nm). HPLC Conditions: Zorbax C-18, gradient 30-80% B in 25 min, flow: 1 mL/min, 25° C., A: 0.1% TFA in H$_2$O, B: 0.1% TFA in CH$_3$CN; Chiral Purity: >99% (215 nm), >99% (254 nm), >99% (280 nm), Retention time: 12.9 min; Conditions: Chiralpak AD, 30% IPA/70% hexane. Rotation: $[α]^{16}_D$=+16.5° (c=1.24, MeOH).

Compound 13

R-Methyl3-{{4-[(diethylamino)carbonyl]phenyl}[4-(pyridin-2-ylmethyl)piperazin-1-yl]methyl}phenylcarbamate

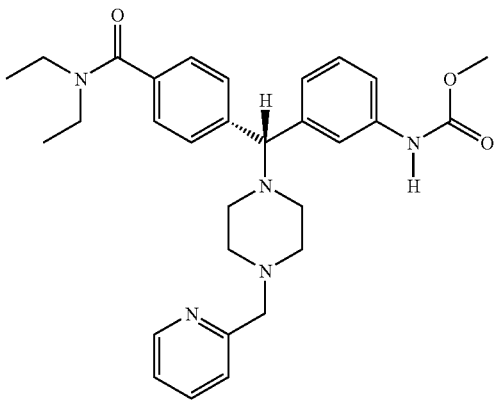

Using the same method as for COMPOUND 1 and using INTERMEDIATE 4a (200 mg, 0.47 mmol) and 2-pyridine carboxaldehyde (76 mg, 0.70 mmol) afforded 187 mg of COMPOUND 13. $^1$H NMR (400 MHz, CD$_3$OD): δ 1.08 (m, 3H), 1.21 (m, 3H), 2.75 (br s, 4H), 3.24 (m, 2H), 3.41 (m, 4H), 3.51 (m, 2H), 3.72 (s, 3H), 4.48 (s, 2H), 4.48 (s, 1H), 7.11 (m, 1H), 7.20 (m, 2H), 7.33 (d, J=8.0 Hz, 2 H), 7.43 (m, 1H), 7.48 (m, 1H), 7.57 (d, J=8.0 Hz, 2 H), 7.73 (s, 1H), 7.89 (s, 1H), 8.66 (m, 1H). Anal. calcd for C$_{30}$H$_{37}$N$_5$O$_3$×1.7 C$_2$HF$_3$O$_2$× 0.8H$_2$O: C, 55.42; H, 5.61; N, 9.67. Found: C, 55.40; H, 5.62; N, 9.83. M.S. (calcd): 516.30 (MH$^+$), M.S. (found): 516.28 (MH$^+$). HPLC: k': 3.02; Purity: >97% (215 nm), >98% (254 nm), >99% (280 nm). HPLC Conditions: Zorbax C-18, gradient 20-50% B in 25 min, flow: 1 mL/min, 25° C., A: 0.1% TFA in H$_2$O, B: 0.1% TFA in CH$_3$CN; Chiral Purity: >99% (215 nm), >99% (254 nm), >99% (280 nm), Retention time: 11.3 min; Chiral HPLC Conditions: Chiralpak AD, 30% IPA/ 70% hexane. Rotation: $[α]^{16}_D$=−15.4° (c=1.01, MeOH).

Compound 14

S-Methyl3-{{4-[(diethylamino)carbonyl]phenyl}[4-(pyridin-4-ylmethyl)piperazin-1-yl]methyl}phenylcarbamate

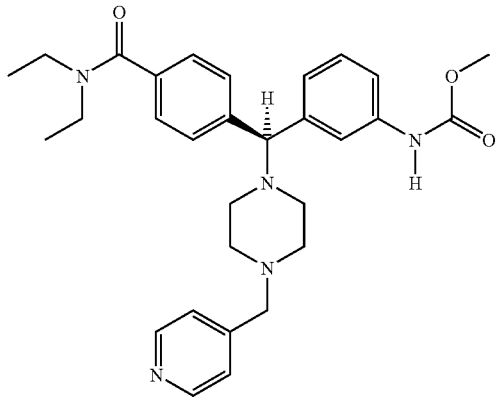

Using the same method as for COMPOUND 1 and using INTERMEDIATE 4b (200 mg, 0.47 mmol) and 4-pyridine carboxaldehyde (76 mg, 0.70 mmol) afforded 217 mg of COMPOUND 14. $^1$H NMR (Free Amine, 400 MHz, CDCl$_3$): δ 1.09 (br s, 3H), 1.21 br s, 3H), 2.43 (m, 8H), 3.24 (br s, 2H), 3.50 (s, 2H), 3.51 (br s, 2H), 3.76 (s, 3H), 4.22 (s, 1H), 6.63 (s, 1H), 7.10 (m, 1H), 7.22 (m, 4H), 7.28 (d, J=8.2 Hz, 2 H), 7.42 (m, 1H), 7.42 (d, J=8.2 Hz, 2 H), 8.52 (s, 2H).

Anal. calcd for C$_{30}$H$_{37}$N$_5$O$_3$×1.9 C$_2$HF$_3$O$_2$×1.8H$_2$O: C, 53.09; H, 5.60; N, 9.16. Found: C, 53.04; H, 5.60; N, 9.18. M.S. (calcd): 516.30 (MH$^+$), M.S. (found): 516.28 (MH$^+$). HPLC: k': 2.69; Purity: >99% (215 nm), >99% (254 nm), >99% (280 nm). HPLC Conditions: Zorbax C-18, gradient 20-50% B in 25 min, flow: 1 mL/min, 25° C., A: 0.1% TFA in H$_2$O, B: 0.1% TFA in CH$_3$CN; Chiral Purity: >99% (215 nm), >99% (254 nm), >99% (280 nm), Retention time: 12.9 min; Chiral HPLC Conditions: Chiralpak AD, 30% IPA/70% hexane. Rotation: $[\alpha]^{16}{}_D$=+10.3° (c=1.25, MeOH).

Compound 15

R-Methyl3-{{4-[(diethylamino)carbonyl]phenyl}[4-(pyridin-4-ylmethyl)piperazin-1-yl]methyl}phenylcarbamate

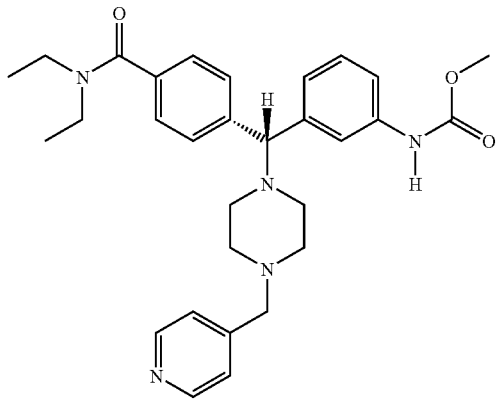

Using the same method as for COMPOUND 1 and using INTERMEDIATE 4a (200 mg, 0.47 mmol) and 4-pyridine carboxaldehyde (76 mg, 0.70 mmol) afforded 247 mg of COMPOUND 15. $^1$H NMR (Free Amine, 400 MHz, CDCl$_3$): δ 1.09 (br s, 3H), 1.21 br s, 3H), 2.45 (m, 8H), 3.24 (br s, 2H), 3.50 (s, 2H), 3.51 (br s, 2H), 3.76 (s, 3H), 4.22 (s, 1H), 6.64 (s, 1H), 7.10 (m, 1H), 7.22 (m, 4H), 7.28 (d, J=8.2 Hz, 2 H), 7.42 (m, 1H), 7.42 (d, J=8.2 Hz, 2 H), 8.52 (d, J=5.7 Hz, 2H). Anal. calcd for C$_{30}$H$_{37}$N$_5$O$_3$×2.6 C$_2$HF$_3$O$_2$×1.0H$_2$O: C, 50.93; H, 5.05; N, 8.44. Found: C, 50.89; H, 5.07; N, 8.50. M.S. (calcd): 516.30 (MH$^+$), M.S. (found): 516.28 (MH$^+$). HPLC: k': 2.69; Purity: >99% (215 nm), >99% (254 nm), >99% (280 nm). HPLC Conditions: Zorbax C-18, gradient 20-50% B in 25 min, flow: 1 mL/min, 25° C., A: 0.1% TFA in H$_2$O, B: 0.1% TFA in CH$_3$CN; Chiral Purity: >99% (215 nm), >99% (254 nm), >99% (280 nm), Retention time: 16.3 min; Conditions: Chiralpak AD, 30% IPA/70% hexane. Rotation: $[\alpha]^{16}{}_D$=-8.1° (c=1.10, MeOH).

Compound 16

R-Methyl3-{{4-[(diethylamino)carbonyl]phenyl}[4-(1,3-thiazol-2-ylmethyl)-piperazin-1-yl]methyl}phenylcarbamate

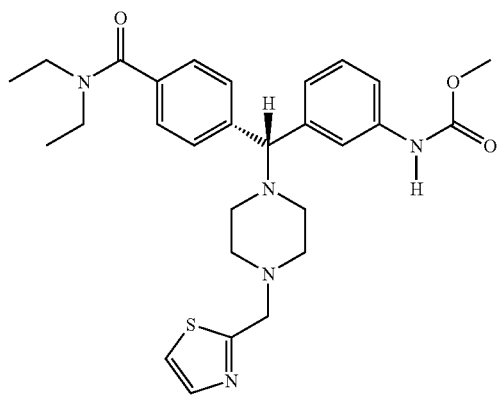

Using the same method as for COMPOUND 1 and using INTERMEDIATE 4a (140 mg, 0.33 mmol) and 2-thiazole carboxaldehyde (45 mg, 0.39 mmol) afforded 85 mg of COMPOUND 16. $^1$H NMR (Free Amine, 400 MHz, CDCl$_3$): δ 1.09 (br s, 3H), 1.21 br s, 3H), 2.44 (br s, 4H), 2.61 (br s, 4H), 3.23 (br s, 2H), 3.51 (br s, 2H), 3.76 (s, 3H), 3.88 (s, 2H), 4.23 (s, 1H), 6.61 (s, 1H), 7.11 (m, 1H), 7.23 (m, 3H), 7.28 (d, J=8.2 Hz, 2 H), 7.41 (m, 1H), 7.43 (d, J=8.2 Hz, 2H) 7.70 (d, J=3.3 Hz, 1 H). M.S. (calcd): 522.3 (MH$^+$), M.S. (found): 522.2 (MH$^+$) HPLC: k': 4.09; Purity: >99% (215 nm), >99% (254 nm), >99% (280 nm). HPLC Conditions: Zorbax C-18, gradient 20-50% B in 25 min, flow: 1 mL/min, 25° C., A: 0.1% TFA in H$_2$O, B: 0.1% TFA in CH$_3$CN; Chiral Purity: >99% (215 nm), >99% (254 nm), >99% (280 nm), Retention time: 9.5 min; Chiral HPLC Conditions: Chiralpak AD, 30% IPA/70% hexane. Rotation: $[\alpha]^{16}{}_D$=-12.08° (c=1.01, MeOH).

Compound 17

[3-[[4-[(diethylamino)carbonyl]phenyl][4-(phenylmethyl)-1-piperazinyl]methyl]phenyl]methyl-carbamic acid, methyl ester

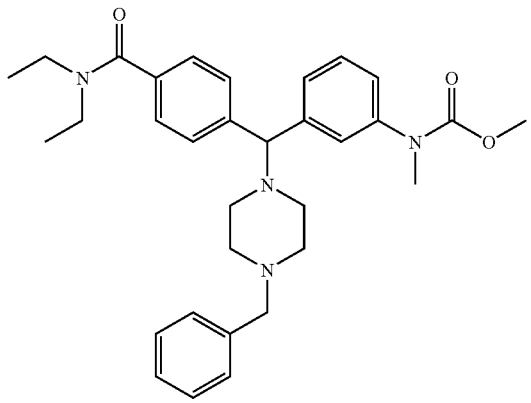

INTERMEDIATE 3 was methylated with sodium hydride/methyl iodide and the Boc group cleaved with TFA. The secondary amine was reacted with benzaldehyde and sodium triacetoxyborohydride to give racemic COMPOUND 17. This material was purified by chiral HPLC on Chiralpak AD 25% EtOH/75% Heptane to yield enantiomerically pure COMPOUND 17. $^1$H NMR (400 MHz, CD$_3$OD): □ 1.09 (m, 3H), 1.22 (m, 3H), 2.31 (m, 2H), 3.05 (m, 2H), 3.25 (m, 4H), 3.25 (s, 3H), 3.40 (m, 2H), 3.51 (m, 2H), 3.83 (s, 3H), 4.34 (s, 2H), 4.50 (s, 1H), 7.15 (m, 1H), 7.32 (m, 4H), 7.43 (s, 1H), 7.49 (s, 5H), 7.55 (d, J=8.2 Hz, 2 H). M.S. (calc'd): 529.3 (MH$^+$), M.S. (found): 529.2 (MH$^+$). HPLC: k': 2.42; Purity: >99% (215 nm), >99% (254 nm), >99% (280 nm). Conditions: Zorbax C-18, gradient 20-50% B in 25 min, flow: 1 mL/min, 25° C., A: 0.1% TFA in H$_2$O, B:0.1% TFA in CH$_3$CN; Chiral Purity: >99% (215 nm)>98% (254 nm)>99% (280 nm), Retention time: 7.01 min; Conditions: Chiralpak AD, 30% IPA/70% hexane. $[\alpha]^{16}_D$=−15.69° (c=1.06, MeOH).

Compound 18

[3-[(S)-[4-[(diethylamino)carbonyl]phenyl][4-(3-pyridinylmethyl)-1-piperazinyl]methyl]phenyl]-carbamic acid, methyl ester

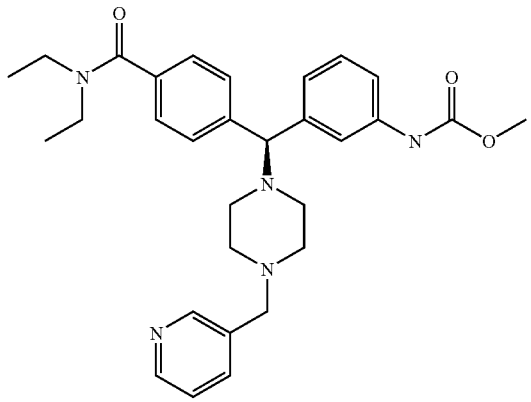

Methyl chloroformate (0.042 mL, 0.54 mmol) and zinc dust (35 mg, 0.54 mmol) were stirred together in 3 mL of dry toluene at room temperature under nitrogen for 10 minutes. A 8 mL toluene solution of INTERMEDIATE 14 (247 mg, 0.54 mmol) was then added dropwise and the reaction mixture was stirred at room temperature for one hour. The solution was then diluted with dichloromethane and filtered. The organic phase washed with saturated NaHCO$_3$ solution, brine and dried over anhydrous Na$_2$SO$_4$. The product was purified by silica gel flash chromatography eluting 30% hexanes in acetone rising to 27% hexanes, 3% methanol in acetone to afford COMPOUND 18. $^1$H NMR (400 MHz, CDCl$_3$) δ1.09 (br s, 3H), 1.21 (br s, 3H), 2.31-2.54 (m, 8H), 3.23 (br s, 2H), 3.47-3.56 (m, 4H), 3.76 (s, 3H), 4.21 (s, 1H), 6.68 (br s, 1H), 7.08 (dt, J=7.21 Hz 1.61 Hz, 1H), 7.18-7.25 (m, 3H), 7.27 (d, J=7.86 Hz, 2H), 7.41 (d, J=8.02 Hz, 2H), 7.64 (dt, J=7.69 Hz 1.92 Hz, 1H), 8.49 (dd, J=4.97 Hz, 1.60 Hz, 1H), 8.52 (d, J=1.76 Hz, 1H). Found: C, 56.47; H, 6.76; N, 10.71. C$_{30}$H$_{37}$N$_5$O$_3$×1.0H$_2$O×2.9 HCl×0.2C$_4$H$_{10}$O has C, 56.55; H, 6.76; N, 10.70%. M.S. (calc'd): 516.3 (MH$^+$), M.S. (found): 516.2 (MH$^+$). HPLC: k': 4.27; Purity: >99% (215 nm), >99% (254 nm), >99% (280 nm). Conditions: Zorbax C-18, gradient 10-50% B in 25 min, flow: 1 mL/min, 25° C., A: 0.1% TFA in H$_2$O, B:0.1% TFA in CH$_3$CN; Chiral Purity: >99% (215 nm)>98% (254 nm)>99% (280 nm), Retention time: 6.66 min; Chiral HPLC Conditions: Chiralpak AD, 50% ethanol/50% hexane. Rotation: $[\alpha]_D$=+7.64° (c=0.497, MeOH).

Compound 19

[3-[(S)-[4-[(diethylamino)carbonyl]phenyl][4-(2-thiazolylmethyl)-1-piperazinyl]methyl]phenyl]-carbamic acid, methyl ester

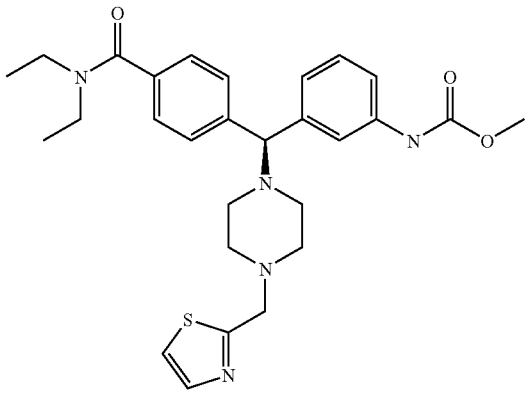

Methyl chloroformate (0.031 mL, 0.40 mmol) and zinc dust (26 mg, 0.40 mmol) were stirred together in 2 mL of dry toluene at room temperature under nitrogen for 10 minutes. A 5 mL toluene solution of INTERMEDIATE 15 (185 mg, 0.40 mmol) was then added dropwise and the reaction mixture was stirred at room temperature for one hour. The solution was then diluted with dichloromethane and filtered. The organic phase washed with saturated NaHCO$_3$ solution, brine and dried over anhydrous Na$_2$SO$_4$. The product was purified by silica gel flash chromatography eluting 30% hexanes in acetone rising to 27% hexanes, 3% methanol in acetone to afford COMPOUND 19. $^1$HNMR (400 MHz, CD$_3$OD) δ 1.06 (t, J=6.49 Hz, 3H), 1.19 (t, J=6.93 Hz, 3H), 2.90-3.10 (m, 2H), 3.17-3.25 (m, 2H), 3.33-3.42 (m, 4H), 3.45-3.52 (m, 2H), 3.70 (s, 3H), 4.59 (s, 2H), 7.16-7.23 (m, 1H), 7.26 (d, J=4.00

Hz, 2H), 7.36 (d, J=7.81 Hz, 2H), 7.65 (d, J=7.32 Hz, 2H), 7.73-7.8 (m, 2H), 7.88-7.93 (m, 1H).

Found: C, 56.81; H, 6.53; N, 11.56. $C_{28}H_{35}N_5O_3S \times 0.90H_2O$ 1.5HCl has C, 56.75; H, 6.51; N, 11.82%. M.S. (calc'd): 522.3 (MH+), M.S. (found): 522.2 (MH+). HPLC: k': 3.99; Purity: >99% (215 nm), >99% (254 nm), >99% (280 nm). Conditions: Zorbax C-18, gradient 20-50% B in 25 min, flow: 1 mL/min, 25° C., A: 0.1% TFA in $H_2O$, B:0.1% TFA in $CH_3CN$; Chiral Purity: >99% (215 nm)>99% (254 nm)>99% (280 nm), Retention time: 20.31 min; Chiral HPLC Conditions: Chiralpak AD, 30% ethanol/70% hexane. Rotation: $[\alpha]_D=+9.13°$ (c=1.06, MeOH).

Compound 20

Methyl 3-{(R)-{4-[(diethylamino)carbonyl]phenyl} [4-(1,3-thiazol-4-ylmethyl)piperazin-1-yl] methyl}phenylcarbamate

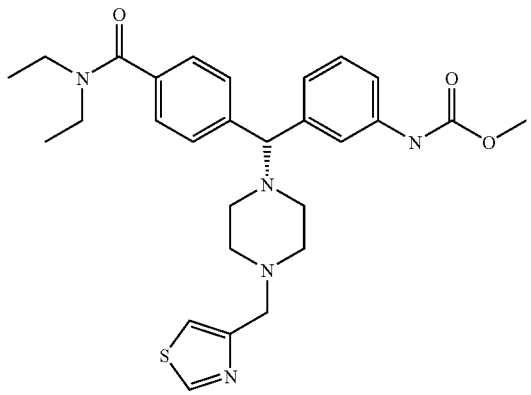

To a solution of optically pure INTERMEDIATE 4a (0.150 g, 0.35 mmol) in 4 ml of DMF was added $K_2CO_3$ (0.122 g, 0.88 mmol) and 4-(chloromethyl)-1,3-thiazole (0.066 g, 0.39 mmol) and the mixture was heated at 60° C. overnight. The solvent was evaporated and the crude material was dissolved in dichloromethane, washed with water then brine. The organic extract was dried over $Na_2SO_4$, filtered and concentrated to give crude product that was purified by reverse phase HPLC (gradient 5-50% $CH_3CN$ in $H_2O$ containing 0.1% TFA) to give COMPOUND 20 (0.030 g, 11.3% yield) as the TFA salt. This material was lyophilized from $CH_3CN/H_2O$ to produce white powder. $^1H$ NMR (400 MHz, $CD_3OD$) δ 1.09 (t, J=6.6 Hz, 3H), 1.22 (t, J=6.8 Hz, 3H), 2.36 (br s., 2H), 3.04 (br s., 2H), 3.19-3.35 (m, 4H), 3.42 (br s., 2H), 3.51 (q, J=6.6 Hz, 2H), 3.72 (s, 3H), 4.45 (s, 1H), 4.52 (s, 2H), 7.10 (dt, J=1.5, 7.0 Hz, 1H), 7.16-7.24 (m, 2H), 7.33 (d, J=8.4 Hz, 2H), 7.56 (d, J=8.2 Hz, 2H), 7.71, (s, 1H), 7.84 (s, 1H), 9.1 (s, 1H). Purity (HPLC): >89% (215 nm), >99% (254 nm), >99% (280 nm); Conditions: Zorbax C-18, gradient: 10-95% B in 25 min, flow: 1 mL/min, 40° C., A—0.1% Formic Acid in $H_2O$, B—0.1% Formic Acid in MeCN; Chiral purity: >99% (215 nm), >99% (254 nm), >99% (280 nm), Retention time 6.67 min; Conditions: Chiralpak AD 50% IPA/50% hexane. Rotation $[\alpha]^{18}_D=-14.7°$ (c=0.88, MeOH)

Compound 21

Methyl 3-{(S)-{4-[(diethylamino)carbonyl]phenyl} [4-(1,3-thiazol-4-ylmethyl)piperazin-1-yl] methyl}phenylcarbamate

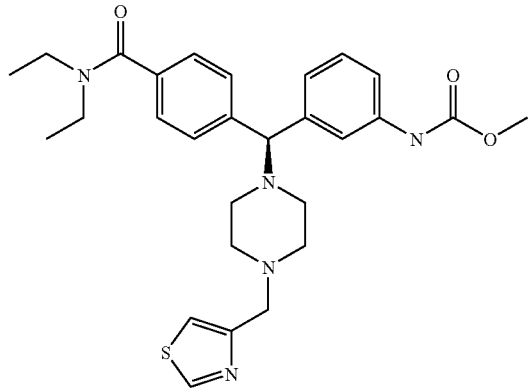

To a solution of optically pure INTERMEDIATE 4b (0.225 g, 0.53 mmol) in 4 ml of DMF was added $K_2CO_3$ (0.183 g, 1.33 mmol) and 4-(chloromethyl)-1,3-thiazole (0.099 g, 0.58 mmol) and the mixture was heated at 60° C. overnight. The solvent was evaporated and the crude material was dissolved in dichloromethane, washed with water then brine. The organic extract was dried over $Na_2SO_4$, filtered and concentrated to give crude product that was purified by reverse phase HPLC (gradient 5-50% $CH_3CN$ in $H_2O$ containing 0.1% TFA) to give COMPOUND 21 (0.166 g, 41.7% yield) as the TFA salt. This material was lyophilized from $CH_3CN/H_2O$ to produce white powder. $^1H$ NMR (400 MHz, $CD_3OD$) δ 0.97 (t, J=7.2 Hz, 3H), 1.11 (t, J=6.8 Hz, 3H), 2.25 (br s., 2H), 2.91 (br s., 2H), 3.07-3.21 (m, 4H), 3.31 (br s., 2H), 3.41 (q, J=6.8 Hz, 2H), 3.61 (s, 3H), 4.34 (s, 1H), 4.41 (s, 2H), 6.99 (dt, J=1.6, 7.0 Hz, 1H), 7.05-7.13 (m, 2H), 7.22 (d, J=8.2 Hz, 2H), 7.45 (d, J=8.2 Hz, 2H), 7.60 (s, 1H), 7.74 (d, J=2.0 Hz, 1H), 8.99 (d, J=2.0 Hz, 1H), 9.13 (s, 1H).

Anal. calcd for $C_{28}H_{35}N_5O_3S \times 1.8TFA \times 1.1H_2O$: C, 50.83; H, 5.26; N, 9.38. Found: C, 50.82; H, 5.23; N, 9.33. MS (calcd): 552.2 (MH+), MS (found): 552.2 (MH+). Purity (HPLC): >99% (215 nm), >99% (254 nm), >99% (280 nm); Conditions: Zorbax C-18, gradient: 10-95% B in 25 min, flow: 1 mL/min, 40° C., A—0.1% Formic Acid in $H_2O$, B—0.1% Formic Acid in MeCN; Chiral purity: >99% (215 nm), >99% (254 nm), >99% (280 nm), Retention time 6.66 min; Conditions: Chiralpak AD 50% IPA/50% hexane. Rotation $[\alpha]^{18}_D=+14.5°$ (c=1.07, MeOH)

Compound 22

Methyl 3-{(R)-{4-[(diethylamino)carbonyl]phenyl} [4-(1,3-thiazol-5-ylmethyl)piperazin-1-yl] methyl}phenylcarbamate

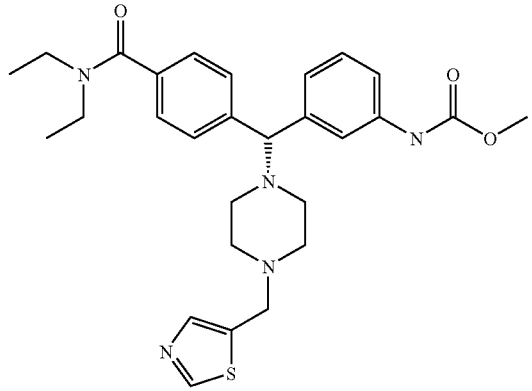

To a solution of INTERMEDIATE 4a (0.163 g, 0.38 mmol) in 1,2 dichloroethane (6 ml) was added thiazole-5-carboxaldehyde (0.087 g, 0.77 mmol) and NaHB(OAc)$_3$ (0.163 g, 0.77 mmol). The reaction was stirred overnight at room temperature and was quenched with saturated aqueous NaHCO$_3$. The layers were separated and the aqueous layer was extracted with dichloromethane (2×15 mL). The combined organic layers were washed with H$_2$O, brine, then dried over Na$_2$SO$_4$, filtered, concentrated and purified by reverse phase HPLC (gradient 5-50% CH$_3$CN in H$_2$O containing 0.1% TFA) to give COMPOUND 22 (0.205 g, 71.2% yield) as the TFA salt. This material was lyophilized from CH$_3$CN/H$_2$O to produce a pale yellow solid. $^1$H NMR (400 MHz, CD$_3$OD) δ 1.09 (t, J=6.8 Hz, 3H), 1.22 (t, J=6.8 Hz, 3H), 2.77 (br s., 4H), 3.18-3.40 (m, 6H), 3.51 (q, J=7.0 Hz, 2H), 3.72 (s, 3H), 4.56 (s, 1H), 4.63 (s, 2H), 7.12 (dt, J=1.9, 8.4 Hz, 1H), 7.19 (dt, J=1.95, 8.4 Hz, 1H), 7.21-7.26 (m, 1H), 7.34 (d, J=8.4 Hz, 2H), 7.57 (d, J=8.2 Hz, 2H), 7.74 (s, 1H), 8.05 (s, 1H), 9.17 (s, 1H). Anal. calcd for C$_{28}$H$_{35}$N$_5$O$_3$S×2.6TFA×0.3H$_2$O: C, 48.42; H, 4.68; N, 8.50.

Found: C, 48.49; H, 4.83; N, 8.30. MS (calcd): 552.2 (MH+), MS (found): 552.2 (MH+). Purity (HPLC): >99% (215 nm), >99% (254 nm), >99% (280 nm); Conditions: Zorbax C-18, gradient: 10-95% B in 25 min, flow: 1 mL/min, 40° C., A—0.1% Formic Acid in H$_2$O, B—0.1% Formic Acid in MeCN; Chiral purity: >99% (215 nm), >99% (254 nm), >99% (280 nm), Retention time 9.92 min; Conditions: Chiralpak AD 50% IPA/50% hexane. Rotation [α]$^{18}$$_D$=−12.4° (c=1.01, MeOH).

Compound 23

Methyl 3-{(S)-{4-[(diethylamino)carbonyl]phenyl}[4-(1,3-thiazol-5-ylmethyl)piperazin-1-yl]methyl}phenylcarbamate

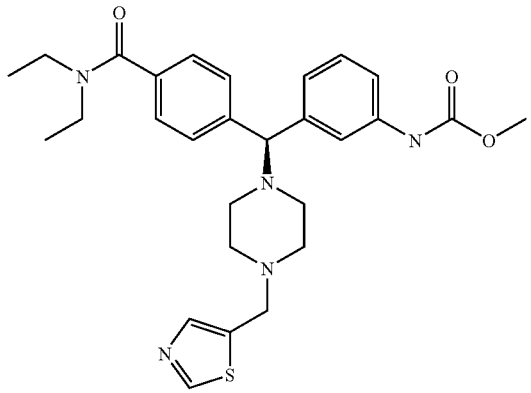

To a solution of INTERMEDIATE 4b (0.223 g, 0.53 mmol) in 1,2 dichloroethane (8 ml) was added thiazole-5-carboxaldehyde (0.119 g, 1.05 mmol) and NaHB(OAc)$_3$ (0.223, 1.05 mmol). The reaction was stirred overnight and quenched with saturated aqueous NaHCO$_3$. The layers were separated and the aqueous phase was extracted with dichloromethane (2×15 mL). The combined organic extracts were washed with H$_2$O, brine, dried over Na$_2$SO$_4$, filtered, concentrated and purified by reverse phase HPLC (gradient 5-50% CH$_3$CN in H$_2$O containing 0.1% TFA) to give COMPOUND 23 (0.214 g, 54.2% yield) as the TFA salt. This material was lyophilized from CH$_3$CN/H$_2$O to produce a yellow solid. $^1$H NMR (400 MHz, CD$_3$OD) δ 1.09 (t, J=6.3 Hz, 3H), 1.22 (t, J=6.6 Hz, 3H), 2.52 (br s., 2H), 2.97 (br s., 2H), 3.18-3.40 (m, 6H), 3.51 (q, J=6.8 Hz, 2H), 3.72 (s, 3H), 4.56 (s, 1H), 4.64 (s, 2H), 7.11 (dt, J=1.56, 7.4 Hz, 1H), 7.17-7.21 (m, 1H), 7.21-7.26 (m, 1H), 7.35 (d, J=8.2 Hz, 2H), 7.57 (d, J=8.4 Hz), 7.74 (s, 1H), 8.05 (s, 1H), 9.17 (s, 1H). Purity (HPLC): >98% (215 nm), >99% (254 nm), >99% (280 nm); Conditions: Zorbax C-18, gradient: 10-95% B in 25 min, flow: 1 mL/min, 40° C., A—0.1% Formic Acid in H2O, B—0.1% Formic Acid in MeCN; Chiral purity: >99% (215 nm), >99% (254 nm), >99% (280 nm), Retention time 13.26 min; Conditions: Chiralpak AD 50% IPA/50% hexane. Rotation [α]$^{18}$$_D$=+12.7° (c=0.97, MeOH).

What is claimed is

1. A method for the therapy of anxiety in a warm-blooded animal, comprising: administering to said animal in need of such therapy a therapeutically effective amount of a compound according to formula I, or a pharmaceutically acceptable salt, diastereomer, or enantiomer thereof, or mixtures thereof:

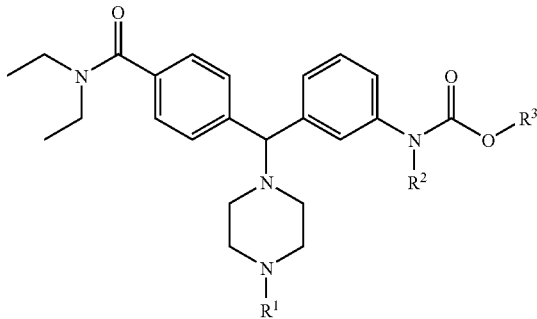

wherein
  $R^1$ is —H or —CH$_2$—$R^4$;
  $R^2$ is —H or C$_{1-3}$alkyl;
  $R^3$ is C$_{1-6}$alkyl or C$_{3-6}$cycloalkyl; and
  $R^4$ phenyl; pyridyl; thienyl; furyl; imidazolyl; triazolyl; pyrrolyl; thiazolyl; or N-oxido-pyridyl, wherein said phenyl; pyridyl; thienyl; furyl; imidazolyl; triazolyl; pyrrolyl; thiazolyl; and N-oxido-pyridyl are optionally substituted with one or more groups selected from C$_{1-6}$alkyl, halogenated C$_{1-6}$alkyl, —NO$_2$, —CF$_3$, C$_{1-6}$alkoxy, chloro, fluoro, bromo, and iodo.

2. A method according to claim 1, wherein
  $R^1$ is —CH$_2$—$R^4$;
  $R^2$ is —H or C$_{1-3}$alkyl;
  $R^3$ is C$_{1-6}$alkyl or C$_{3-6}$cycloalkyl; and
  $R^4$ phenyl; pyridyl; thienyl; furyl; imidazolyl; triazolyl; pyrrolyl; thiazolyl; or N-oxido-pyridyl, wherein said phenyl; pyridyl; thienyl; furyl; imidazolyl; triazolyl; pyrrolyl; thiazolyl; and N-oxido-pyridyl are optionally substituted with one or more groups selected from C$_{1-6}$alkyl halogenated C$_{1-6}$alkyl —NO$_2$, —CF$_3$, C$_{1-6}$alkoxy chloro, fluoro, bromo, and iodo.

3. A method according to claim 2, wherein
  $R^4$ is phenyl; pyridyl; thienyl; furyl; imidazolyl; pyrroly; or thiazolyl;
  $R^2$ is —H or methyl; and
  $R^3$ is methyl; ethyl; propyl; or isopropyl.

4. A method according to claim 1, wherein
  $R^1$ is —H;
  $R^2$ is —H or C$_{1-3}$alkyl; and
  $R^3$ is C$_{1-6}$alkyl or C$_{3-6}$cycloalkyl.

5. A method according to claim 1, wherein the compound according to formula I is selected from:
  Methyl 3-[(4-[(diethylamino)carbonyl]phenyl)(4-benzyl-piperazin-1-yl)methyl]phenylcarbamate;

Methyl-3-{{4-[(diethylamino)carbonyl]phenyl}[4-(thien-2-ylmethyl)piperazin-1-yl]methyl}phenylcarbamate;

Methyl 3-{{4-[(diethylamino)carbonyl]phenyl}[4-(thien-3-ylmethyl)piperazin-1-yl]methyl}phenylcarbamate;

Methyl 3-{{4-[(diethylamino)carbonyl]phenyl}[4-(2-furylmethyl)piperazin-1-yl]methyl}phenylcarbamate;

Methyl 3-{{4-[(diethylamino)carbonyl]phenyl}[4-(3-furylmethyl)piperazin-1-yl]methyl}phenylcarbamate;

Methyl 3-{{4-[(diethylamino)carbonyl]phenyl}[4-(1H-imidazol-2-ylmethyl)piperazin-1-yl]methyl}phenylcarbamate;

Methyl 3-{{4-[(diethylamino)carbonyl]phenyl}[4-(pyridin-2-ylmethyl)piperazin-1-yl]methyl}phenylcarbamate;

Methyl 3-{{4-[(diethylamino)carbonyl]-phenyl}[4-(pyridin-4-yl-methyl)piperazin-1-yl}methyl}phenylcarbamate;

Methyl 3-{{4-[(diethylamino)carbonyl]phenyl}[4-(1,3-thiazol-2-ylmethyl)-piperazin-1-yl]methyl}phenylcarbamate;

[3-[[4-[(diethylamino)carbonyl]phenyl][4-(phenylmethyl)-1-piperazinyl]methyl]phenyl]-carbamic acid methyl ester;

[3-[(S)-[4-[(diethylamino)carbonyl]phenyl][4-(3-pyridinylmethyl)-1-piperazinyl]methyl]phenyl]-carbamic acid, methyl ester;

[3-[(S)-[4-[(diethylamino)carbonyl]phenyl][4-(2-thiazolylmethyl)-1-piperazinyl]methyl]phenyl]-carbamic acid, methyl ester;

Methyl 3-{(R)-{4-[(diethylamino)carbonyl]phenyl}[4-(1,3-thiazol-4-ylmethyl)piperazin-1-yl]methyl}phenylcarbamate;

Methyl 3-{(S)-{4-[(diethylamino)carbonyl]phenyl}[4-(1,3-thiazol-4-ylmethyl)piperazin-1-yl]methyl}phenylcarbamate;

Methyl 3-{(R)-{4-[(diethylamino)carbonyl]phenyl}[4-(1,3-thiazol-5-ylmethyl)piperazin-1-yl]methyl}phenylcarbamate;

Methyl 3-{(S)-{4-[(diethylamino)carbonyl]phenyl}[4-(1,3-thiazol-5-ylmethyl)piperazin-1-yl]methyl}phenylcarbamate; and

[3-[[4-[(diethylamino)carbonyl]phenyl]-1-piperazinylmethyl]phenyl]-carbamic acid, methyl ester; and enantiomers and pharmaceutically acceptable salts thereof.

* * * * *